US007811778B2

(12) United States Patent
Goldenring

(10) Patent No.: US 7,811,778 B2
(45) Date of Patent: Oct. 12, 2010

(54) METHODS OF SCREENING FOR GASTROINTESTINAL CANCER

(75) Inventor: James R. Goldenring, Nashville, TN (US)

(73) Assignee: Vanderbilt University, Nashville, TN (US)

(*) Notice: Subject to any disclaimer, the term of this patent is extended or adjusted under 35 U.S.C. 154(b) by 45 days.

(21) Appl. No.: 11/850,555

(22) Filed: Sep. 5, 2007

(65) Prior Publication Data

US 2008/0057514 A1 Mar. 6, 2008

Related U.S. Application Data

(60) Provisional application No. 60/824,678, filed on Sep. 6, 2006.

(51) Int. Cl.
*G01N 33/574* (2006.01)
(52) U.S. Cl. .......................... 435/7.23; 435/7.1; 435/6
(58) Field of Classification Search ........................ None
See application file for complete search history.

(56) References Cited

U.S. PATENT DOCUMENTS

| | | | |
|---|---|---|---|
| 6,107,048 | A | 8/2000 | Goldenring et al. |
| 6,235,474 | B1 | 5/2001 | Feinberg |
| 6,372,439 | B2 | 4/2002 | Goldenring et al. |
| 6,773,890 | B2 | 8/2004 | Goldenring et al. |
| 2001/0014459 | A1 | 8/2001 | Goldenring et al. |
| 2002/0187487 | A1 | 12/2002 | Goldenring et al. |
| 2003/0077675 | A1 | 4/2003 | Das |
| 2003/0108965 | A1 | 6/2003 | Schummer et al. |
| 2003/0170649 | A1 | 9/2003 | Haas et al. |
| 2004/0033502 | A1* | 2/2004 | Williams et al. ............... 435/6 |
| 2004/0235008 | A1 | 11/2004 | Sementchenko et al. |
| 2005/0009067 | A1 | 1/2005 | Logsdon et al. |
| 2005/0260639 | A1* | 11/2005 | Nakamura et al. ............. 435/6 |
| 2006/0105333 | A1 | 5/2006 | Nakamura et al. |
| 2006/0269921 | A1* | 11/2006 | Segara et al. .................... 435/6 |
| 2009/0208514 | A1* | 8/2009 | Nakamura et al. ........ 424/174.1 |

OTHER PUBLICATIONS

Zhu et al, Biochim Biophys Res Commun, 2000, 273:1019-1024.*
Noguchi et al, Proc American Assoc Cancer Res Annual Meeting, Mar. 2004, 45:792.*
Labouvie et al, J Cancer Res Clin Oncol, 1999, 125:71-76.*
Nomura, et al., Spasmolytic Polypeptide Expressing Metaplasia to Preneoplasia in H. felis-Infected Mice, Gastroenterology, 2004, pp. 582-594, 127.
Galgano, et al., Comprehensive Analysis of HE4 Expression In Normal And Malignant Human Tissues, Modern Pathology, 2006, pp. 847-853, 19.
Halldorsdottir, et al., Spasmolytic polypeptide-expressing metaplasias (SPEM) associated with gastric cancer in Iceland, Digestive diseases and sciences, Mar. 2003, 48 (3), pp. 431-441.
Lee, et al, Differential protein analysis of spasomolytic polypeptide expressing metaplasias using laser capture microdissection and two-dimensional difference gel electrophoresis, AIMM, Jun. 2003, 11 (2), pp. 188-193.
Looijenga LH, Gillis AJ, van Gurp RJ, Verkerk AJ, Oosterhuis JW, X Inactivation in Human Testicular Tumors, XIST Expression and Androgen Receptor Methylation Status, Am J Pathol 1997; 151: 581-590.
Yamaguchi, et al., Association of spasmolytic polypeptide-expressing metaplasias with carcinogen administration and oxyntic atrophy in rats, Laboratory investigation; a journal of technical methods and pathology, Aug. 2002; 82 (* ), pp. 1045-1052.
Yamaguchi, et al., Identification of spasmolytic polypeptide expressing metaplasias (SPEM) in remnant gastric cancer and surveillance postgastrectomy biopsies, Digestive diseases and sciences, Mar. 2002, 47 (3), pp. 573-580.
Chow, et al. Characterization of expression at the human XIST locus in somatic, embryonal carcinoma, and transgenic cell lines, Genomics, Sep. 2003, 82(3), pp. 309-322.
Aitola M, Sadek CM, Gustafsson JA, Pelto-Huikko M. Aint/Tacc3 is highly expressed in proliferating mouse tissues during development, spermatogenesis, and oogenesis. J Histochem Cytochem 2003;51:455-69.
Beauchamp RD, Barnard JA McCutchen CM, Cherner JA, Coffey RJ, Jr. Localization of transforming growth factor alpha and its receptor in gastric mucosal cells. J.Clin.Invest. 1989;84:1017-1023.
Biankin, A.V., Kench, J.G., Dijkman, F.P., Biankin, S.A., and Henshall, S.M. Molecular pathogenesis of precursor lesions of pancreatic ductal adenocarcinoma. Pathology 2003;35:14-24.
Bingle L, Singleton V, Bingle CD. The putative ovarian tumour marker gene HE4 (WFDC2), is expressed in normal tissues and undergoes complex alternative splicing to yield multiple protein isoforms. Oncogene 2002;21:2768-73.
Blaser, M., and Parsonnet, J. Parasitism by the bacterium Helicobacter pylori leads to altered gastric homeostasis and neoplasia. J.Clin.Invest. 1994;94:4-8.
Bouchard, D., Morisset, D., Bourbonnais, Y., and Tremblay, G.M. Proteins with whey-acidic-protein motifs and cancer. Lancet Oncol 2006;7:167-174.
Braun KA, Breeden LL. Nascent transcription of MCM2-7 is important for nuclear localization of the minichromosome maintenance complex in G1. Mol Biol Cell 2007;18:1447-56.
Cameron, A.J., Lomboy, C.T., Pera, M., and Carpenter, H.A. Adenocarcinoma of the esophagogastric junction and Barrett's esophagus. Gastroenterology 1995;109:1541-1546.

(Continued)

*Primary Examiner*—Misook Yu
*Assistant Examiner*—Mark Halvorson
(74) *Attorney, Agent, or Firm*—Stites & Harbison PLLC; Mandy Wilson Decker

(57) ABSTRACT

Methods for diagnosing an upper gastrointestinal (GI) cancer in a subject by determining an amount of one or more biomarkers in a biological sample from the subject are provided. Methods for determining whether to initiate or continue prophylaxis or treatment of an upper GI cancer in a subject by determining any measurable change in the amounts of the at least one biomarker in each of a series of biological samples provided over a time period are also provided.

24 Claims, 11 Drawing Sheets

OTHER PUBLICATIONS

Correa P, A human Model of Gastric Carcinogenesis, Cancer Res 1988; 48:3554-3560.

Dhar, D.K., Wang, T.C., Maruyama, R., Udagawa, J., Kubota, H., Fuji, T., Tachibana, M., Ono, T., Otani, H., and Nagasue, N. Expression of cytoplasmic TFF2 is a biomarker of tumor metastasis and negative prognostic factor in gastric cancer. Lab Invest 2003;83:1343-1352.

Dinis-Ribeiro M, da Costa-Pereira A, Lopes C, Barbosa J, Guilherme M, Moreira-Dias L, Lomba-Viana H, Silva R, Abreu N, Lomba-Viana R. Validity of serum pepsinogen I/II ratio for the diagnosis of gastric epithelial dysplasia and intestinal metaplasia during the follow-up of patients at risk for intestinal-type gastric adenocarcinoma. Neoplasia 2004; 6(5):449-56.

El-Zimaity, HMT, Ota, H, Graham, DY, Akamatsu, T, and Katsuyama, T. Patterns of gastric atrophy in intestinal type gastric carcinoma, Cancer 2002;94: 1428-36.

Filipe, M.I., Munoz, N., Matko, I., Kato, I., Pome-Kim, V., Juersek, A., Teuchmann, S., Benz, M., Prijon, T. Intestinal metaplasia types and the risk of gastric cancer: a cohort study in Slovenia, Int J Cancer. 1994;57: 324-329.

Fox JG, Li X, Cahill RJ, Andrutis K, Rustgi AK, Odze R, Wang TC, Hypertrophic Gastropathy in Helicobacter felis-infected Wild Type C57BL16 Mice and p53 Hemizygous Transgenic Mice, Gastroenterology 1996; 110:155-166.

Goldenring JR, Poulsom R, Ray GS, Wright NA, Meise KS, Coffey RJ, Expression of Trefoil Peptides in the Gastric Mucosa of Transgenic Mice Overexpressing Transforming Growth Factor-a, Growth Factors 1996; 13:111-119.

Goldenring JR, Ray GS, Coffey RJ, Meunier PC, Haley P J, Barnes TB, Car BD, Reversible Drug-induced Xxyntic Atrophy in Rats, Gastroenterology 2000; 118:1080-1093.

Haggitt RC, Barrett's Esophagus, Dysplasia, and Adenocarcinoma, Hum Pathol 1994;25:982-993.

Hattori, T. Development of adenocarcinomas in the stomach. Cancer 1986;57:1528-1534.

Hellstrom, I., Raycraft, J., Hayden-Ledbetter, M., Ledbetter, J.A., Schummer, M., McIntosh, M., Drescher, C., Urban, N., and Hellstrom, K.E. The HE4 (WFDC2) protein is a biomarker for ovarian carcinoma. Cancer Res 2003;63:3695-3700.

Houghton J, Stoicov C, Nomura S, Carlson J, Li H, Rogers AB, Fox JG, Goldenring JR, Wang TC. Gastric cancer originating from bone marrow derived cells. Science 2004;In Press.

Karam SM, Leblond CP. Dynamics of epithelial cells in the corpus of the mouse stomach. III. Inward migration of neck cells followed by progressive transformation into zymogenic cells. Anat.Rec. 1993;236:297-313.

Kuipers EJ, Exploring the Link Between Helicobacter pylori and Gastric Cancer, Aliment Pharmacol Ther 1999; 13:3-11.

Leys CM, Nomura S, Rudzinski E, Kaminishi M, Montgomery E, Washington MK, Goldenring JR. Expression of Pdx-1 in human gastric metaplasia and gastric adenocarcinoma. Hum Pathol 2006;37:1162-8.

Means AL, Meszoely IM, Suzuki K, Miyamoto Y, Rustgi AK, Coffey RJ, Jr., Wright CV, Stoffers DA, Leach SD. Pancreatic epithelial plasticity mediated by acinar cell transdifferentiation and generation of nestin-positive intermediates. Development 2005;132:3767-76.

Mills JC, Andersson N, Hong CV, Stappenbeck TS, Gordon JI, Molecular Characterization of Mouse Gastric Epithelial Progenitor Cells, Proc Natl Acad Sci USA 2002; 99:14819-14824.

Nam KT, Varro A, Coffey RJ, Goldenring JR. Potentiation of oxyntic atrophy-induced gastric metaplasia in amphiregulin-deficient mice. Gastroenterology 2007;132:1804-19.

Nomura, S., Settle, S.H., Leys, C., Means, A.L., Peek, R.M., Jr., Leach, S.D., Wright, C.V.E., Coffey, R.J., and Goldenring, J.R. Evidence for repatterning of the gastric fundic epithelium associated with Menetrier's disease and TGFa overexpression. Gastroenterology 2005;128:1292-1305.

Nomura, S., Yamaguchi, H., Wang, T.C., Lee, J.R., and Goldenring, J.R. Alterations in gastric mucosal lineages induced by acute oxyntic atrophy in wild type and gastrin deficient mice. Amer.J.Physiol. 2004;288:G362-G375.

Ogawa, M., Nomura, S., Wang, T.C., and Goldenring, J.R. Altered metaplastic response of waved-2 EGF receptor mutant mice to acute oxyntic atrophy. Am J Physiol 2006;290:G793-G804.

Oishi Y, Kiyohara Y, Kubo M, Tanaka K, Tanizaki Y, Ninomiya T, Doi Y, Shikata K, Yonemoto K, Shirota T, Matsumoto T, Iida M. The serum pepsinogen test as a predictor of gastric cancer: the Hisayama study. Am J Epidemiol. 2006;163 (7):629-37.

Parsonnet J, Friedman GD, Vandersteen DP, Chang Y, Vogelman JH, Orentreich N, Sibley RK. Helicobacter pylori infection and the risk of gastric cancer. New Eng.J.Med. 1991;325:1127-1131.

Pisani P, Bray F, Parkin DM. Estimates of the world-wide prevalence of cancer for 25 sites in the adult population. Int J Cancer 2002;97:72-81.

Ramsey VG, Doherty JM, Chen CC, Stappenbeck TS, Konieczny SF, Mills JC. The maturation of mucus-secreting gastric epithelial progenitors into digestive-enzyme secreting zymogenic cells requires Mist1. Development 2007;134:211-22.

Rindi G, Buffa R, Sessa F, Tortora O, Solcia E. Chromogranin A, Band C, Immunoreactivities of Mammalian Endocrine Cells, Distribution, Distinction from Costored Hormones/Prohormones and Relationship with the Argyrophil Component of Secretory Granules. Histochemistry 1986; 85:19-28.

Schmidt PH, Lee JR, Joshi V, Playford RJ, Poulsom R, Wright NA, Goldenring JR, Identification of a Metaplastic Cell Lineage Associated with Human Gastric Adenocarcinoma, Lab Invest 1999; 79: 639-646.

Smith VC, Genta RM, Role of Helicobacter pylori Gastritis in Gastric Atrophy, Intestinal Metaplasia and Gastric Neoplasia, Microsc Res Tech 2000; 48:313-320.

Stepan V, Ramamoorthy S, Nitsche H, Zavros Y, Merchant JL, Todisco A. Regulation and function of the sonic hedgehog signal transduction pathway in isolated gastric parietal cells. J Biol Chem 2005;280:15700-8.

Wang TC, Dangler CA, Chen D, Goldenring JR, Koh T, Raychowdhury R, Coffey RJ, Ito S, Varro A, Dockray GJ, Fox JG, Synergistic Interaction Between Hypergastrinemia and Helicobacter Infection in a Mouse Model of Gastric Cancer, Gastroenterology 2000; 118:36-47.

Wang TC, Goldenring JR, Dangler C, Ito S, Mueller A, Jeon WK, Koh T J, Fox JG, Mice Lacking Secretory Phospholipase A2 Show Altered Apoptosis and Differentiation with Helicobacter felis Infection, Gastroenterology 1998; 114:675-689.

Zhang B, Kirov S, Snoddy J. WebGestalt: an integrated system for exploring gene sets in various biological contexts. Nucleic Acids Res 2005;33:W741-8.

Zhu L, Shi G, Schmidt CM, Hruban RH, Konieczny SF. Acinar cells contribute to the molecular heterogeneity of pancreatic intraepithelial neoplasia. Am J Pathol 2007;171:263-73.

Ganesan, et al.; Association of BRCA1 with the inactive X chromosome and XIST RNA; Phil. Trans. R. Soc. Lond. B; 2004; 359:123-128.

Huang, et al.; Relationship of XIST expression and responses of ovarian cancer to chemotherapy; Moleculare Cancer Therapeutics; 2002; 1:769-776.

Kawakami, et al.; The roles of supernumerical X chromosomes and XIST expression in testicular germ cell tumors; 2003; 169:1546-1552.

Kawakami, et al.; XIST unmethylated DNA fragments in male-derived plasma as a tumor marker for testicular cancer; Lancet; 2004; 363:40-42.

* cited by examiner

METHODS OF SCREENING FOR GASTROINTESTINAL CANCER

RELATED APPLICATIONS

The presently-disclosed subject matter claims the benefit of U.S. Provisional Patent Application Ser. No. 60/824,678, filed Sep. 6, 2006; the disclosure of which is incorporated herein by reference in its entirety.

GOVERNMENT INTEREST

This presently-disclosed subject matter was made with U.S. Government support under Grant No. P50 CA95103 awarded by the National Institute of Health (NIH) through the National Cancer Institute Specialized Programs of Research Excellence (NCI SPORE). Thus, the U.S. Government has certain rights in the presently-disclosed subject matter.

TECHNICAL FIELD

The presently-disclosed subject matter relates to screening methods for the risk or presence of cancer in a subject. In particular, the presently-disclosed subject matter relates to screening methods for the risk or presence of upper gastrointestinal cancer in a subject.

BACKGROUND

Upper gastrointestinal (GI) cancer, including gastric cancer, esophageal cancer, and pancreatic cancer, is a prominent worldwide cause of malignant disease and mortality. Indeed, gastric cancer is one of the leading causes of cancer-related deaths worldwide, and is the leading cause of cancer-related deaths in Asia.

The pathway to gastric carcinogenesis is mediated through global changes in the lineages of the stomach. Studies over the past 15 years have demonstrated that the major primary cause of gastric cancer in humans is chronic infection with particular sub-classes of the bacterium, *Helicobacter pylori*. See Blaser, M., and Parsonnet, J. 1994. Parasitism by the bacterium *Helicobacter pylori* leads to altered gastric homeostasis and neoplasia. *J. Clin. Invest.* 94:4-8; and Parsonnet, J, Friedman, G D, Vandersteen, D P, Chang, Y, Vogelman, J H, Orentreich, N, and Sibley, R K, 1991. Helicobacter pylori infection and the risk of gastric cancer, *N Engl J Med* 325: 1127-31. Such findings prompted the World Health Organization to designate *H. pylori* as a Class I carcinogen.

Two factors contributing to the evolution of gastric cancer in the presence of chronic *H. pylori* infection are the following: (1) the infection elicits a prominent inflammatory response throughout the gastric mucosa; and (2) chronic infection leads to toss of glandular lineages in the gastric fundus, especially acid-secreting parietal cells and pepsin-secreting chief cells. Whether focal or global, oxyntic atrophy, or the loss of parietal cells, appears as a prerequisite for the development of gastric cancer. See El-Zimaity, H M T, Ota, H, Graham, D Y, Akamatsu, T, and Katsuyama, T, 2002. Patterns of gastric atrophy in intestinal type gastric carcinoma, *Cancer* 94: 1428-36.

The loss of parietal cells leads to emergence of metaplastic lineages within the gastric mucosa that are predisposed to neoplastic transformation. Following on oxyntic atrophy, subjects may show varying levels of foveolar hyperplasia. This increase in surface cell numbers is likely a reactive response to increases in gastrin release secondary to hypochlorhydria. Oxyntic atrophy also leads to mucous cell metaplasia. Studies over the last decade have increasingly emphasized the association of precedent mucous cell metaplasias with the development of upper gastrointestinal cancers in the esophagus, pancreas and stomach.

Development of esophageal cancer is closely linked with Barrett's epithelial metaplasia and pancreatic adenocarcinoma arises from discrete mucous cell metaplasias. See Biankin, A. V., Kench, J. G., Dijkman, F. P., Biankin, S. A., and Henshall, S. M. 2003. Molecular pathogenesis of precursor lesions of pancreatic ductal adenocarcinoma. *Pathology* 35:14-24; and Cameron, A. J., Lomboy, C. T., Pera, M., and Carpenter, H. A. 1995. Adenocarcinoma of the esophagogastric junction and Barrett's esophagus. *Gastroenterology.* 109: 1541-1546.

While the association of cancer with cell atrophy and inflammation is now accepted, the intervening cellular events that mediate the progression from atrophy to neoplasia are not entirely clear. Also, while the association of upper GI-type cancers with chronic *H. pylori* infection and oxyntic atrophy is accepted, the connections between discrete metaplasias and cancer are less clear. Further studies may provide insight into these details.

With regard to mortality and morbidity associated with upper GI cancer, both have been lowered due to early diagnosis through screening. Rigorous upper endoscopic surveillance is currently considered to be the most effective screening method; however, the process is invasive, unpleasant, time-consuming, and costly. Accordingly, there remains a need in the art for an effective screening method to identify risk of upper GI cancer in subjects, which overcomes the drawbacks associated with currently-available screening methods.

SUMMARY

This Summary lists several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter addresses the above-identified problems, and others, by providing in some embodiments a method for diagnosing an upper gastrointestinal (GI) cancer in a subject by determining an amount of one or more biomarkers in a biological sample from the subject. The presently-disclosed subject matter further provides in some embodiments, a method for determining whether to initiate or continue prophylaxis or treatment of an upper GI cancer in a subject by determining any measurable change in the amounts of the at least one biomarker in each of a series of biological samples provided over a time period.

The one or more biomarkers can be, but are not limited to the following biomarkers: HE4 (human epididymis protein 4, WFDC2); LGALS3 (lectin: galactose binding, soluble 3): IL1RN (interleukin 1 receptor antagonist); TRIP13 (thyroid hormone receptor interactor 13); FIGNL1 (fidgetin-like 1); CRIP1 (cysteine-rich protein 1, intestinal); S100A4 (S100 calcium-binding protein A4); EXOSC8 (exosome component 8); EXPI (extracellular proteinase inhibitor, WDNM1); BRRN1 (barren homolog, *Drosophila*); NELF (nasal embryonic LHRH factor); EREG (epiregulin); TMEM40 (transmembrane protein 40); and TMEM109 (transmembrane protein 109). In some embodiments, the methods further comprise determining an amount in the sample of a TFF2 (trefoil factor 2) biomarker.

In some embodiments, the biological sample comprises blood, serum, plasma, gastric secretions, an upper GI biopsy sample, microdissected cells from an upper GI biopsy, upper GI cells sloughed into the GI lumen, and upper GI cells recovered from stool. In some embodiments, the subject is human. In some embodiments, determining the amount of the at least one biomarker comprises one or more techniques known in the art, including RNA measuring assays and a protein measuring assays. Exemplary RNA measuring assays include RNA hybridization probe microarrays and quantitative polymerase chain reaction (PCR) assays (e.g., quantitative real-time PCR). Exemplary protein measuring assays include mass spectrometry (MS) analysis and immunoassay analysis.

The methods can be used as an alternative to more invasive procedures, or they can be used to prescreen subjects to determine which subjects should proceed with additional procedures, i.e., differentiate between subjects who need not be subjected to additional procedures, and subjects who would benefit from additional and/or more frequent procedures.

The presently-disclosed subject matter further includes in some embodiments kits for diagnosing an upper GI cancer in a subject. The kits comprise in some embodiments probes for selectively binding each of the one or more biomarkers disclosed herein. The probes can be bound to a substrate. The probes can be RNA hybridization probes in some embodiments, which can comprise polynucleotides that selectively bind each of the one or more biomarkers. In other embodiments, the probes are antibodies that selectively bind the biomarkers. In some embodiments, the probes are labeled to allow for detecting the binding of the probes to the one or more biomarkers. For example, in some embodiments, binding of a probe to a biomarker is detected using an enzyme-linked antibody.

Accordingly, it is an object of the presently-disclosed subject matter to methods of screening for upper GI cancer in a subject. This object is achieved in whole or in part by the presently-disclosed subject matter.

An object of the presently-disclosed subject matter having been stated hereinabove, and which is achieved in whole or in part by the presently-disclosed subject matter, other objects and advantages will become evident to those of ordinary skill in the art after a study of the following description of the presently-disclosed subject matter, drawings, and non-limiting examples.

BRIEF DESCRIPTION OF THE DRAWINGS

FIG. 3A is a series of photomicrographs showing immunostaining of HE4 in gastrin knockout mice treated for 0, 1, 3, or 7 days with DMP-777, which pictures show the upregulation of expression in cells at the bases of fundic glands. FIG. 3B is a series of photomicrographs showing immmunostaining of HE4 in normal fundus, SPEM, and goblet cell intestinal metaplasia, which pictures show that normal human stomach does not show HE4 staining, while SPEM and intestinal metaplasia show HE4 staining.

FIG. 4A shows fundic mucosa from an untreated gastrin deficient mouse that was dual immunostained for Mist1 (green, light staining in gray scale photo) and TFF2 (red, dark staining in gray scale photo). Mist1 antibodies stained the nuclei of mature chief cells at the base of fundic glands (lower portion of photo), while TFF2 was positive in mucous neck cells in the neck region of the fundic gland (upper portion of photo). No discernible dual staining cells were observed (Scale bar: 50 μm), FIGS. 4B and 4C show Mist1 and TFF2 expression in a gastrin-deficient mouse treated with DMP-777 for 3 days. The number of Mist1 immunoreactive cells (green, light staining in gray scale photo) decreased in the bottom of glands, and a number of the Mist1 positive cells were dual immunoreactive for TFF2 (red, dark staining in gray scale photo). (Scale bar: 4B, 50 μm; 4C, 10 μm) The high power view in 4C demonstrates the presence of cells dual labeled for Mist1 and TFF2 (arrows). FIG. 4D shows mucosa from an untreated mouse stained with antibodies for the H/K-ATPase (blue, medium staining in gray scale photo), TFF2 (red, dark staining in gray scale photo) and intrinsic factor (green, light staining in gray scale photo). Note that there was no overlap in the staining of the three lineages (Scale bar: 20 μm). FIGS. 4E and 4F show mucosa from a mouse treated with DMP-777 for 3 days stained with antibodies for the H/K ATPase (blue, medium staining in gray scale photo), TFF2 (red, dark staining in gray scale photo) and intrinsic factor (green, light staining in gray scale photo). White parietal cells only stained with H/K-ATPase antibodies, SPEM cells at the base of the glands stained for both intrinsic factor (green, light staining in gray scale photo) and TFF2 (red, dark staining in gray scale photo). The higher power view in FIG. 4F demonstrates the presence of two separate populations of vesicles in the SPEM cells. (Scale bar: 4E, 10 μm; 4F, 4 μm). FIGS. 4G, 4H, and 4I show electron micrographs of chief cells from an untreated mouse (FIG. 4G) and emerging SPEM cells from a 3 day DMP-777-treated mouse (FIGS. 4H and 4I). In FIG. 4G, chief cells showed uniformly staining zymogen granules (Scale bar, 2 μm). As shown in FIGS. 4H and 4I, SPEM cells at the base of fundic glands of a mouse treated with DMP-777 for 3 days contained a heterogeneous set of granule morphologies. (Scale bar, 4G and 4H, 2 μm: 4I, 1 μm).

As shown in FIG. 6F, quantification of MCM3 and Ki-67 staining showed a significant increase in MCM3 staining at days 3-14 of treatment (green line, shown as light gray line in gray scale figure p<0.01, *p<0.001). Ki-67 staining (red line, shown as black line in gray scale figure) showed a smaller increase, which was only significant at 7 days of treatment (*p<0.05).

FIGS. 7A and 7B are photomicrographs showing MCM3 positive cells in untreated mice are chief cells. Section from an untreated mouse stained with antibody against MCM3 (red, dark staining in gray scale photo, noted with arrows), antibody against intrinsic factor (green, light staining in gray scale photo) and DAPI (blue, medium staining in gray scale photo). The image of cells at the base of fundic glands in FIG. 7A shows dual MCM3 staining with DAPI, while FIG. 7B is a triple overlay image. MCM3 positive cells at the bases of fundic glands were also stained for Intrinsic factor (arrows), indicating their identification as chief cells (Scale bar: 10 μm).

As shown in FIG. 9A, little immunoreactivity for HE4 was detectable in the normal gastric mucosa of untreated gastrin-deficient mice. As shown in FIG. 9B, prominent staining is visible for HE4 in SPEM in a gastrin deficient mouse treated with DMP-777, As shown in FIG. 9C, strong staining for HE4 was observed in SPEM in the mucosa of a C57BL/6 mouse infected with *Helicobacter felis* for 9 months. As shown in FIG. 9D, no staining for HE4 was observed in the normal human gastric fundic mucosa. As shown in FIG. 9AE, SPEM from a human subject stained strongly with HE4. As shown in FIG. 9F, SPEM and goblet cell intestinal metaplasia both stained for HE4 in a region of metaplastic transition. As shown in FIGS. 9G and 9H, in sections containing both SPEM and intestinal metaplasia HE4 immunoreactivity was present in both metaplasias. As shown in FIG. 9I, intestinal metaplasia showed strong positivity for HE4.

FIGS. 10A-10D are photomicrographs of well to moderately differentiated gastric cancers. Note the prominent expression of HE4 in intestinal type gastric adenocarcinoma. FIGS. 10E-10G are photomicrographs of poorly-differentiated gastric cancers. Although the majority of poorly differentiated or diffuse cancers did not show immunoreactivity a minority of tumors did show positivity. FIGS. 10H-10I are photomicrographs of signet ring-cell type gastric adenocarcinomas. The strongest HE4 positivity was observed in signet ring adenocarcinomas.

BRIEF DESCRIPTION OF THE SEQUENCE LISTING

Figure 1:
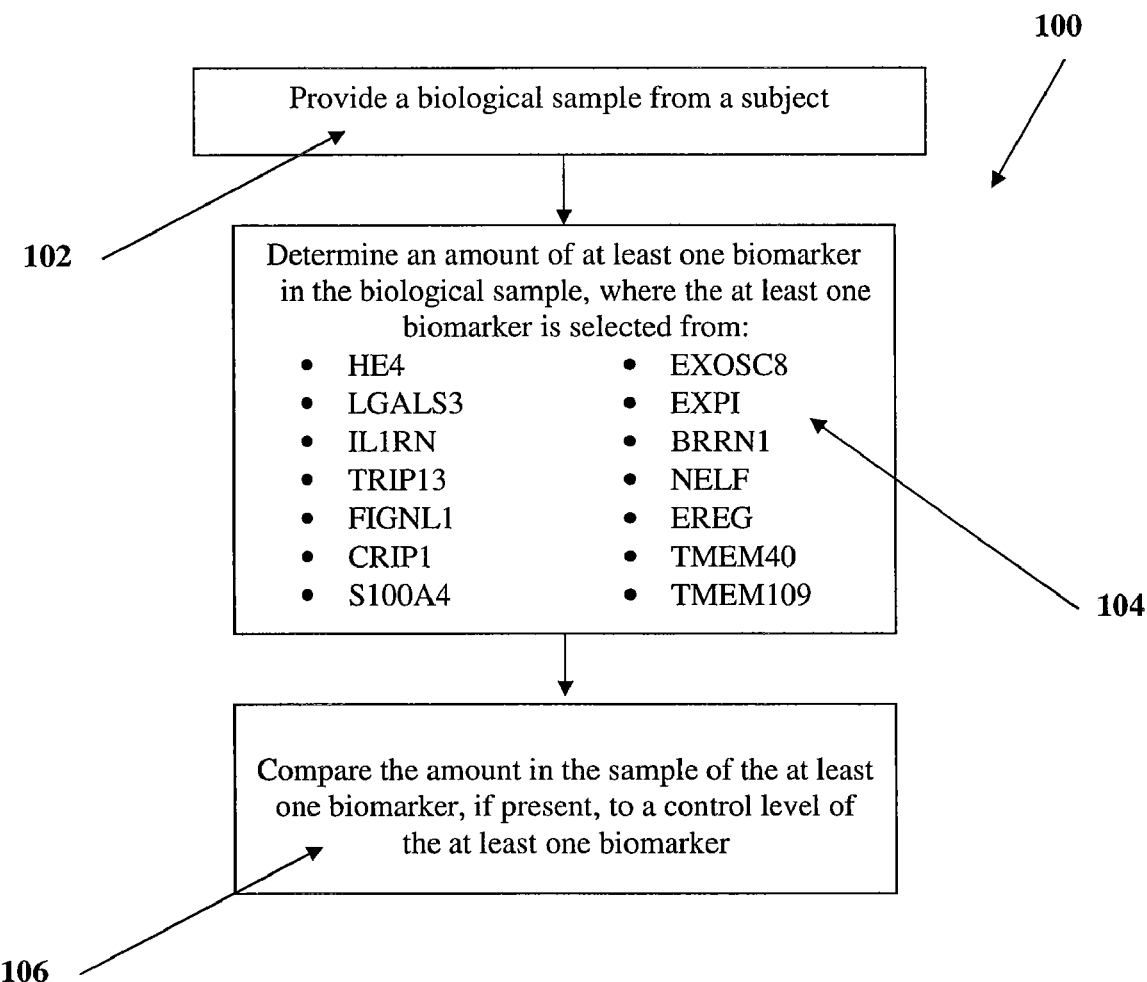
FIG. 1 is a flow chart illustrating the steps involved in an exemplary method for screening for upper GI cancer.

SEQ ID NOS: 1 and 2 are PCR sense and antisense primers specific for GAPDH, respectively.

SEQ ID NOS: 3 and 4 are PCR sense and antisense primers specific for MCM3, respectively.

SEQ ID NOS: 5 and 6 are PCR sense and antisense primer specific for MCM5, respectively, SEQ ID NOS: 7 and 8 are PCR sense and antisense primers specific for MCM7, respectively.

SEQ ID NOS. 9 and 10 are PCR sense and antisense primers specific for ST3GAL6, respectively.

SEQ ID NOS: 11 and 12 are PCR sense and antisense primers specific for ATF3, respectively.

SEQ ID NOS: 13 and 14 are PCR sense and antisense primers specific for HE4, respectively.

SEQ ID NOS: 15 and 16 are PCR sense and antisense primers specific for IL1RN, respectively.

SEQ ID NOS: 17 and 18 are PCR sense and antisense primers specific for TFF2, respectively.

DETAILED DESCRIPTION

The details of one or more embodiments of the presently-disclosed subject matter are set forth in the accompanying description below. Other features, objects, and advantages of the presently-disclosed subject matter will be apparent from the specification, drawings, and claims. All publications, patent applications, patents, and other references mentioned herein are incorporated by reference in their entirety. Some of the polynucleotide and polypeptide sequences disclosed herein are cross-referenced to GENBANK® or other public database accession numbers. The sequences cross-referenced in the GENBANK® or other public databases are expressly incorporated by reference as are equivalent and related sequences present in GENBANK® or other public databases. Also expressly incorporated herein by reference are all annotations present in the GENBANK® database associated with the sequences disclosed herein. Also incorporated herein by this reference are U.S. Pat. Nos. 6,773,890; 6,372,439; and 6,107,048 to Goldenring et at. In case of conflict, the present specification, including definitions, will control.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Upper gastrointestinal (GI) cancers remain a leading cause of cancer-related death worldwide. While the discrete mechanisms of carcinogenesis remain obscure, one constant in the etiology of these cancers is a sequence of lineage changes in the involved cells. For example, gastric cancer develops in part through the loss of acid secreting parietal cells from the fundic mucosa, or oxyntic atrophy. The loss of parietal cells leads to alterations in the cells in the gastric mucosa with the emergence of metaplastic mucous cell lineages. The development of oxyntic atrophy and gastric cancer in humans are strongly linked through a sequence of lineage changes from normal to metaplastic to neoplastic (Parsonnet J, Friedman G D, Vandersteen D P, Chang Y, Vogelman J H, Orentreich N, Sibley R K. *Helicobacter pylori* infection and the risk of gastric cancer. New Eng.J.Med. 1991; 325:1127-1131). Along with the cell lineage alteration, changes also occur in the expression of cellular protein biomarkers.

"Upper GI cancer", as the term is used herein, refers to neoplasms or malignant tumors found in the upper GI tract of animal subjects, which includes the mouth, pharynx, esophagus, and stomach(s) of animals, as well as associated organs, including the pancreas and gall bladder. Exemplary upper GI cancers include, but are not limited to gastric cancers, pancreatic cancers, and esophageal cancers.

The presently-disclosed subject matter provides for the identification of biomarkers for upper GI cancer that can be measured in a subject to diagnose an upper GI cancer. For example, and as disclosed in detail in the Examples, it has now been determined that in mice the WAP domain protein HE4 is not expressed in the normal stomach, but is strongly expressed in spasmolytic polypeptide/TFF2-expressing metaplasia (SPEM) from mice, as well as in both SPEM and intestinal metaplasia in humans. As disclosed herein, HE4 was expressed in the vast majority of intestinal type and signet ring gastric adenocarcinomas studied (see Examples). The results disclosed herein indicate that SPEM develops from transdifferentiation of chief cells. Furthermore, this metaplastic transition is associated with expression of other important secreted biomarkers relevant to the process of pre-neoplasia, which are disclosed herein and can also be utilized as part of the diagnostic methods of the present subject matter.

As such, the presently-disclosed subject matter provides in some embodiments methods for diagnosing an upper GI cancer in a subject by determining an amount of one or more biomarkers associated with the cancer in a biological sample provided from the subject. Exemplary biomarkers associated with upper GI cancer that can be used in the diagnostic methods disclosed herein include, but are not limited to: HE4 (human epididymis protein 4; also referred to as WFDC2); LGALS3 (lectin, galactose binding, soluble 3); IL1RN (interleukin 1 receptor antagonist); TRIP13 (thyroid hormone receptor interactor 13); FIGNL1 (fidgetin-like 1), CRIP1 (cysteine-rich protein 1, intestinal); S100A4 (S100 calcium-binding protein A4); EXOSC8 (exosome component 8); EXPI (extracellular proteinase inhibitor; also referred to as WDNM1); BRRN1 (barren homolog 1; also referred to as NCAPH); NELF (nasal embryonic LHRH factor); EREG (epiregulin); TMEM40 (transmembrane protein 40); and TMEM 109 (transmembrane protein 109). In some embodiments, in addition to the one or more biomarkers disclosed above, the biomarker trefoil factor 2 (TFF2), which has been associated with cancers of the GI tract and associated organs, can be screened to determine an amount of the TFF2 in the biological sample.

Table 1 provides further description of exemplary human biomarkers (with the exception of EXPI, wherein the mouse biomarker is disclosed) associated with upper GI cancers, including gene loci and accession ID numbers for mRNAs encoding the biomarker polypeptides. However, the exemplary human biomarkers are not intended to limit the present subject matter to human biomarkers, or even mRNA biomarkers only. Rather, the present subject matter encompasses biomarkers across animal species that are associated with upper GI cancers. In addition, standard gene/protein nomenclature guidelines generally stipulate human gene name abbreviations are capitalized and italicized and protein name abbreviations are capitalized, but not italicized. Further, standard gene/protein nomenclature guidelines generally stipulate mouse, rat, and chicken gene name abbreviations italicized with the first letter only capitalized and protein name abbreviations capitalized, but not italicized. In contrast, the gene/protein nomenclature used herein when referencing specific biomarkers uses all capital letters for the biomarker abbreviation, but is intended to be inclusive of genes (including mRNAs and cDNAs) and proteins across animal species.

A "biomarker" is a molecule useful as an indicator of a biologic state in a subject. With reference to the present subject matter, the biomarkers disclosed herein can be polypeptides that exhibit a change in expression or state, which can be correlated with the risk of developing, the presence of, or the progression of upper GI cancers in a subject. In addition, the biomarkers disclosed herein are inclusive of messenger RNAs (mRNAs) encoding the biomarker polypeptides, as measurement of a change in expression of an mRNA can be correlated with changes in expression of the polypeptide encoded by the mRNA. As such, determining an amount of a biomarker in a biological sample is inclusive of determining an amount of a polypeptide biomarker and/or an amount of an mRNA encoding the polypeptide biomarker either by direct or indirect (e.g., by measure of a complementary DNA (cDNA) synthesized from the mRNA) measure of the mRNA.

TABLE 1

| Biomarker | Human Gene Locus | Accession ID No. (mRNA) |
|---|---|---|
| HE4 (WFDC2) | 20q12-q13.2 | X63187 |
| LGALS3 | 14q22.3 | NM_002306 |
| IL1RN | 2q14.2 | M55646 |
| TRIP13 | 5p15 | L40384 |
| FIGNL1 | 7p12.2 | AK023142 |
| CRIP-1 | 14q32.33 | NM_001311 |
| S100A4 | 1q12-q22 | NM_002961 |
| EXOSC8 | 13q13.1 | NM_181503 |
| EXPI (WDNM1) | *Mus musculus** | NM_007969 |
| BRRN1 (NCAPH) | 2q11.2 | NM_015341 |
| NELF | 9q34.3 | NM_015537 |
| EREG | 4q21.21 | D30783 |
| TMEM 40 | 3p25.2 | NM_018306 |
| TMEM 109 | 11q12.2 | NM_024092 |

*Mouse gene provided. Human homolog not confirmed.

The terms "polypeptide", "protein", and "peptide", which are used interchangeably herein, refer to a polymer of the 20 protein amino acids, including modified amino acids (e.g., phosphorylated, glycated, etc.), regardless of size or function.

Although "protein" is often used in reference to relatively large polypeptides, and "peptide" is often used in reference to small polypeptides, usage of these terms in the art overlaps and vanes. The term "peptide" as used herein refers to peptides, polypeptides, proteins and fragments of proteins, unless otherwise noted. The terms "protein", "polypeptide" and "peptide" are used interchangeably herein when referring to a gene product and fragments thereof. Thus, exemplary polypeptides include gene products, naturally occurring proteins, homologs, orthologs, paralogs, fragments and other equivalents, variants, and fragments of the foregoing.

The terms "polypeptide fragment" or "fragment", when used in reference to a polypeptide, refers to a polypeptide in which amino acid residues are absent as compared to the full-length polypeptide itself, but where the remaining amino acid sequence is usually identical to the corresponding positions in the reference polypeptide. Such deletions can occur at the amino-terminus or carboxy-terminus of the reference polypeptide, or alternatively both.

A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, 30, 40, 50, or up to 100 or more residues. Further, fragments can include a sub-fragment of a specific region, which sub-fragment retains a function of the region from which it is derived. When the term "peptide" is used herein, it is intended to include the full-length peptide as well as fragments of the peptide. Thus, an identified fragment of a peptide (e.g., by mass spectrometry or immunoassay) is intended to encompass the fragment as well as the full-length peptide. As such, determining an amount of a biomarker in a sample can include determining an amount of the full-length biomarker polypeptide, modified variants, and/or fragments thereof.

In some embodiments of the presently-disclosed subject matter, a method for diagnosing an upper GI cancer in a subject is provided. The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a biomarker, the amount (including presence or absence) of which is indicative of the presence, severity, or absence of the condition.

Along with diagnosis, clinical cancer prognosis is also an area of great concern and interest. It is important to know the aggressiveness of the cancer cells and the likelihood of tumor recurrence in order to plan the most effective therapy. If a more accurate prognosis can be made or even a potential risk for developing the cancer assessed, appropriate therapy and in some instances less severe therapy for the patient can be chosen. Measurement of cancer biomarkers can be useful in order to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers disclosed herein. Further, in some embodiments of the presently disclosed subject matter, multiple determination of the biomarkers over time can be made to facilitate diagnosis and/or prognosis. A temporal change in the biomarker can be used to predict a clinical outcome, monitor the progression of the upper GI cancer and/or efficacy of appropriate therapies directed against the cancer. In such an embodiment for example, one might expect to see a decrease in the amount of one or more biomarkers disclosed herein (and potentially one or more additional biomarker(s), if monitored, including but not limited to TFF2) in a biological sample over time during the Course of effective therapy.

The presently disclosed subject matter further provides in some embodiments a method for determining whether to initiate or continue prophylaxis or treatment of a cancer in a subject. In some embodiments, the method comprises providing a series of biological samples over a time period from the subject; analyzing the series of biological samples to determine an amount of at least one biomarker disclosed herein in each of the biological samples; and comparing any measurable change in the amounts of one or more of the biomarkers in each of the biological samples. Any changes in the amounts of biomarkers over the time period can be used to predict risk of developing cancer, predict clinical outcome, determine whether to initiate or continue the prophylaxis or therapy of the cancer, and whether a current therapy is effectively treating the cancer. For example, a first time point can be selected prior to initiation of a treatment and a second time point can be selected at some time after initiation of the treatment. Biomarker levels can be measured in each of the samples taken from different time points and qualitative and/or quantitative differences noted. A change in the amounts of the biomarker levels from the different samples can be correlated with upper GI cancer risk, prognosis, determining treatment efficacy, and/or progression of the cancer in the subject.

The terms "correlated" and "correlating," as used herein in reference to the use of diagnostic and prognostic the biomarkers disclosed herein, refers to comparing the presence or quantity of the biomarker in a subject to its presence or quantity in subjects known to suffer from, or known to be at risk of, a given condition (e.g., an upper GI cancer); or in subjects known to be free of a given condition, i.e. "normal subjects" or "control subjects". For example, a level of one or more biomarkers disclosed herein in a biological sample can be compared to a biomarker levels determined to be associated with a specific type of cancer. The sample's biomarker level is said to have been correlated with a diagnosis; that is, the skilled artisan can use the biomarker level to determine whether the subject suffers from a specific type of cancer, and respond accordingly. Alternatively, the sample's biomarker level can be compared to a control biomarker level known to be associated with a good outcome (e.g., the absence of cancer), such as an average level found in a population of normal subjects.

In certain embodiments, a diagnostic or prognostic biomarker is correlated to a condition or disease by merely its presence or absence. In other embodiments, a threshold level of a diagnostic or prognostic biomarker can be established, and the level of the indicator in a subject sample can simply be compared to the threshold level.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of cancer, or a given prognosis.

Likewise, a decrease in the marker from the initial time to the second time can be indicative of a particular type or severity of cancer, or a given prognosis. Furthermore, the degree of change of one or more markers can be related to the severity of the cancer and future adverse events.

The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

The phrase "determining the prognosis" as used herein refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the presence, absence or levels of a biomarker. Instead, the skilled artisan will understand that the term "prognosis" refers to an increased probability that a certain course or outcome will occur, that is, that a course or outcome is more likely to occur in a subject exhibiting a given condition, when compared to those individuals not exhibiting the condition. For example, in individuals not exhibiting the condition (e.g., not expressing the biomarker or expressing it at a reduced level), the chance of a given outcome (e.g., suffering from an upper GI cancer) may be very low (e.g., <1%), or even absent. In contrast, in individuals exhibiting the condition (e.g., expressing the biomarker or expressing it at a level greatly increased over a control level), the chance of a given outcome (e.g., suffering from an upper GI cancer) may be high. In certain embodiments, a prognosis is about a 5% chance of a given expected outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome is a statistical analysis. For example, a biomarker level (e.g., quantity of a biomarker in a sample) of greater than a control level in some embodiments can signal that a subject is more likely to suffer from a cancer than subjects with a level less than or equal to the control level, as determined by a level of statistical significance. Additionally, a change in marker concentration from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the level of a prognostic or diagnostic biomarker disclosed herein can be established, and the degree of change in the level of the indicator in a biological sample can simply be compared to the threshold degree of change in the level. A preferred threshold change in the level for markers of the presently disclosed subject matter is about 5%, about 10%, about 15%, about 20%, about 25%, about 30%, about 50%, about 75%, about 100%, and about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

The "amount" of a biomarker determined from a sample refers to a qualitative (e.g., present or not in the measured sample), quantitative (e.g., how much is present), or both measurement of the biomarker. The "control level" is an amount (including the qualitative presence or absence) or range of amounts of the biomarker found in a comparable biological sample in subjects free of an upper GI cancer, or at least free of the upper GI cancer of interest being tested. As one non-limiting example of calculating the control level, the amount of biomarker present in a normal biological sample can be calculated and extrapolated for whole subjects.

With reference to FIG. 1, an exemplary non-limiting method of the present subject matter for diagnosing an upper GI cancer in a subject is now disclosed. The exemplary method 100 includes, providing a biological sample from the subject 102; determining an amount of at least one biomarker in the biological sample, where the at least one biomarker is selected from, HE4, LGALS3, IL1RN, TRIP13, FIGNL1, CRIP1, S100A4, EXOSC8, EXPI, BRRN1, NELF, EREG, TMEM40, and TMEM 109 104; and comparing the amount in the sample of the at least one biomarker, if present, to a control level of the at least one biomarker 106. The subject is then diagnosed as having an upper GI cancer if there is a measurable difference in the amount of the at least one biomarker in the sample as compared to the control level.

With regard to the step of providing a biological sample from the subject 102, different types of biological samples can be provided and used in the exemplary method 100. For example, a serum, plasma, or blood sample can be provided. For another example, gastric secretions can be provided. For still further examples, the following biological samples can be provided: an upper GI biopsy sample (e.g., from the stomach), microdissected cells from an upper GI biopsy; upper GI cells sloughed into the GI lumen; and upper GI cells recovered from stool. Methods for obtaining the preceding samples from a subject are generally known in the art.

Turning now to the step of determining an amount of at least one biomarker in the biological sample 104, various methods known to those skilled in the art can be used to identify the one or more biomarkers in the provided biological sample. In some embodiments, determining the amount of the at least one biomarker comprises using an RNA measuring assay to measure mRNA encoding biomarker polypeptides in the sample and/or using a protein measuring assay to measure amounts of biomarker polypeptides in the sample.

In certain embodiments of the method, the amounts of biomarkers can be determined by probing for mRNA of the biomarker in the sample using any RNA identification assay known to those skilled in the art. Briefly, RNA can be extracted from the sample, amplified, converted to cDNA, labeled, and allowed to hybridize with probes of a known sequence, such as known RNA hybridization probes (selective for mRNAs encoding biomarker polypeptides) immobilized on a substrate (e.g., an array or microarray) or quantitated by real time PCR (e.g., quantitative real-time PCR, such as available from Bio-Rad Laboratories, Hercules, Calif., U.S.A.). Because the probes to which the nucleic acid molecules of the sample are bound are known, the molecules in the sample can be identified. In this regard, DNA probes for one or more of HE4, LGALS3, IL1RN, TRIP13, FIGNL1, CRIP1, S100A4, EXOSC8, EXPI, BRRN1, NELF, EREG, TMEM40, and TMEM109 can be immobilized on a substrate and provided for use in practicing a method in accordance with the present subject matter.

With regard to determining amounts of biomarker polypeptides in samples, mass spectrometry and/or immunoassay devices and methods can be used, although other methods are well known to those skilled in the art as well, See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526, 5,525,524, and 5,480,792, each of which is hereby incorporated by reference in its entirety. Immunoassay devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, can be employed to determine the presence or amount of analytes without the need for a labeled molecule. See, e.g., U.S. Pat. Nos. 5,631,171; and 5,955,377, each of which is hereby incorporated by reference in its entirety.

Thus, in certain embodiments of the presently-disclosed subject matter, biomarker peptides are analyzed using an immunoassay. The presence or amount of a biomarker peptide disclosed herein can be determined using antibodies or fragments thereof specific for each biomarker polypeptide, or fragment thereof, and detecting specific binding. For example, in some embodiments, the antibody specifically binds HE4, LGALS3, IL1RN, TRIP13, FIGNL1, CRIP1, S100A4, EXOSC8, EXPI, BRRN1, NELF, EREG, TMEM40, or TMEM109, which is inclusive of antibodies that bind the full-length peptides or a fragment thereof. In some embodiments, the antibody is a monoclonal antibody.

Any suitable immunoassay can be utilized, for example, enzyme-linked immunoassays (ELISA), radioimmunoassays (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies or fragments thereof specific for the markers is also contemplated by the presently-disclosed subject matter. The antibodies can be immobilized onto a variety of solid supports, such as magnetic or chromatographic matrix particles, the surface of an assay plate (such as microtiter wells), pieces of a solid substrate material (such as plastic, nylon, paper), and the like. An assay strip can be prepared by coating the antibody or a plurality of antibodies in an array on a solid support. This strip can then be dipped into the test biological sample and then processed quickly through washes and detection steps to generate a measurable signal, such as for example a colored spot.

In some embodiments, mass spectrometry (MS) analysis can be used alone or in combination with other methods (e.g., immunoassays or RNA measuring assays) to determine the presence and/or quantity of the one or more biomarkers disclosed herein in a biological sample. In some embodiments, the MS analysis comprises matrix-assisted laser desorption/ionization (MALDI) time-of-flight (TOF) MS analysis, such as for example direct-spot MALDI-TOF or liquid chromatography MALDI-TOF mass spectrometry analysis. In some embodiments, the MS analysis comprises electrospray ionization (ESI) MS, such as for example liquid chromatography (LC) ESI-MS. Mass analysis can be accomplished using commercially-available spectrometers. Methods for utilizing MS analysis, including MALDI-TOF MS and ESI-MS, to detect the presence and quantity of biomarker peptides in biological samples are known in the art. See for example U.S. Pat. Nos. 6,925,389; 6,989,100; and 6,890,763 for further guidance, each of which is incorporated herein by this reference.

Although certain embodiments of the method only call for a qualitative assessment of the presence or absence of the one or more biomarkers in the biological sample, other embodiments of the method call for a quantitative assessment of the amount of each of the one or more markers in the biological sample. Such quantitative assessments can be made, for example, using one of the above mentioned methods, as will be understood by those skilled in the art.

In addition to the specific biomarkers set forth in Table 1, measurements of amounts of other biomarkers useful for diagnosing upper GI cancer can also be provided. For example, the presence of trefoil factor 2 (TFF2) immunoreactive cells is associated with gastric cancers. See Schmidt, P. H., Lee, J. R., Joshi, V., Playford, R. J., Poulsom, R., Wright, N. A., and Goldenring, J. R. 1999. Identification of a metaplastic cell lineage associated with human gastric adenocarcinoma. *Lab.Invest.* 79:639-646 ("Schmidt, et al."). For another example, certain ratios of pepsinogen I/II have been associated with certain upper GI cancers. Lee e.g., Oishi Y, Kiyohara Y, Kubo M, Tanaka K, Tanizaki Y, Ninomiya T, Doi Y, Shikata K, Yonemoto K, Shirota T, Matsumoto T. Iida M. 2006. The serum pepsinogen test as a predictor of gastric cancer: the Hisayama study, *Am J Epidemiol.* 163(7):629-37; and Dinis-Ribeiro M, da Costa-Pereira A, Lopes C, Barbosa J, Guilherme M, Moreira-Dias L, Lomba-Viana H, Silva R, Abreu N, Lomba-Viana R. 2004. Validity of serum pepsinogen I/II ratio for the diagnosis of gastric epithelial dysplasia and intestinal metaplasia during the follow-up of subjects at risk for intestinal-type gastric adenocarcinoma. *Neoplasia* 6(5):449-56. As such, TFF2 and/or pepsinogen I and pepsinogen II (to determine pepsinogen II/I ratios) can be additionally measured to create a diagnostic matrix for identification of those at risk for or presently suffering from upper GI cancer.

In certain embodiments of the method, it may be desirable to include a control sample that is analyzed concurrently with the biological sample, such that the results obtained from the biological sample can be compared to the results obtained from the control sample. Additionally, it is contemplated that standard curves can be provided, with which assay results for the biological sample may be compared. Such standard curves present levels of biomarker as a function of assay units, i.e., fluorescent signal intensity, if a fluorescent label is used. Using samples taken from multiple donors, standard curves can be provided for control levels of the one or more biomarkers in normal tissue, as well as for "at-risk" levels of the one or more biomarkers in tissue taken from donors with metaplasia or from donors with upper GI cancer.

In certain embodiments of the method, a subject is identified as having metaplasia upon identifying in a biological sample obtained from the subject one or more biomarkers selected from: HE4, LGALS3, IL1RN, TRIP13, FIGNL1, CRIP1, S100A4, EXOSC8, EXPI, BRRN1, NELF, EREG, TMEM40, and TMEM109. In other embodiments of the method, the identification of one or more of such biomarkers in a biological sample obtained from the subject results in the subject being identified as having cancer.

Regardless of whether the one or more biomarkers are being identified in the biological samples by measuring biomarker gene-expression, e.g., mRNA, or by directly measuring the protein biomarkers, it is contemplated that the efficacy, accuracy, sensitivity, and specificity of the diagnostic method can be enhanced by probing for multiple biomarkers in the biological sample. For example, in certain embodiments of the method, the biological sample can be probed for TFF2 and a biomarker selected from: HE4, LGALS3, IL1RN, TRIP13, FIGNL1, CRIP1, S100A4, EXOSC8, EXPI, BRRN1, NELF, EREG, TMEM40, and TMEM109. For another example, the biological sample can be probed for 2-5 biomarkers selected from: HE4, LGALS3, IL1RN, TRIP13, FIGNL1, CRIP1, S100A4, EXOSC8, EXPI, BRRN1, NELF, EREG, TMEM40, and TMEM109. For another example, the biologic sample can be probed for 6-10 biomarkers selected from: HE4, LGALS3, IL1RN, TRIP133, FIGNL1, CRIP1, S100A4, EXOSC8, EXPI, BRRN1, NELF, EREG, TMEM40, and TMEM109.

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker levels over time. Increases or decreases in marker levels, as well as the absence of change in marker levels, can provide useful information about the disease status that includes, but is not limited to identifying the approximate time from onset of the event, the presence and amount of salvageable tissue, the appropriateness of drug therapies, the effectiveness of various therapies, and identification of the subjects outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

Referring again to FIG. 1, the subject is diagnosed as having an upper GI cancer if, when compared to a control levee, there is a measurable difference in the amount of the at least one biomarker in the sample 106. Conversely, when no probed biomarker is identified in the biological sample, the subject can be identified as not having upper GI cancer, not being at risk for the cancer, or as having a low risk of the cancer. In this regard, subjects having the cancer or risk thereof can be differentiated from subjects having low to substantially no cancer or risk thereof. Those subjects having a risk of developing an upper GI cancer can be placed on a more intensive and/or regular screening schedule, including upper endoscopic surveillance. On the other hand, those subjects having low to substantially no risk may avoid being subjected to an endoscopy, until such time as a future screening, for example, a screening conducted in accordance with the present subject matter, indicates that a risk of upper GI cancer has appeared in those subjects.

As mentioned above, depending on the embodiment of the method of the present subject matter, identification of the one or more biomarkers can be a qualitative determination of the presence or absence of the biomarkers, or it can be a quantitative determination of the concentration of the biomarkers. In this regard, in the exemplary method, the step of diagnosing the subject as having, or at risk of developing, upper GI cancer indicates that certain threshold measurements are made, i.e., the levels of the one or more biomarkers in the biological sample exceed predetermined control levels 106.

In certain embodiments of the method, the control level is any detectable level of the biomarker. In other embodiments of the method where a control sample is tested concurrently with the biological sample, the predetermined level is the level of detection in the control sample. In other embodiments of the method, the predetermined level is based upon and/or identified by a standard curve. In other embodiments of the method, the predetermined level is a specifically identified concentration, or concentration range. As such, the predetermined level can be chosen, within acceptable limits that will be apparent to those skilled in the art, based in part on the embodiment of the method being practiced and the desired specificity, etc.

Further with respect to the diagnostic methods of the presently disclosed subject matter, a preferred subject is a vertebrate subject. A preferred vertebrate is warm-blooded; a preferred warm-blooded vertebrate is a mammal. A preferred mammal is most preferably a human. As used herein, the term "subject" includes both human and animal subjects. Thus, veterinary therapeutic uses are provided in accordance with the presently disclosed subject matter.

As such, the presently disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs, swine, including pigs, hogs, and wild boars, ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like.

The presently-disclosed subject matter further includes a system for diagnosing an upper GI cancer in a subject. The system can be provided, for example, as a commercial kit that can be used to screen for a risk of upper GI cancer or diagnose an upper GI cancer in a subject from whom a biological sample has been collected. An exemplary system provided in accordance with the present subject matter includes probes for selectively binding each of one or more biomarkers selected from, HE4, LGALS3, IL1RN, TRIP13, FIGNL1, CRIP1, S100A4, EXOSC8, EXPI, BRRN1, NELF, EREG, TMEM40, and TMEM109; and components for detecting the binding of the probes to the one or more biomarkers.

In certain embodiments of the system, the probes can be RNA hybridization probes, in which case the RNA of the biological sample would be isolated, amplified, converted to cDNA, labeled, and incubated with the probes to allow for hybridization. The binding of the probes to the cDNA of the biomarkers can be detected using the label of the probe, which can be, for example, a fluorescent label.

In other embodiments of the system, the probes can be antibodies that selectively bind the protein biomarkers. The binding of the antibodies to the biomarkers can be detected, for example, using an enzyme-linked antibody.

The system can also include certain samples for use as controls. The system can further include one or more standard curves providing levels of biomarker mRNA, or levels of biomarker protein as a function of assay units. The system can additionally include probes for TFF2 and/or probes for pepsinogen I and pepsinogen II (to determine pepsinogen I/II ratios).

Thus, in some embodiments of the presently-disclosed subject matter, a kit for the analysis of biomarkers is provided that comprises probes, including for example antibodies selective for biomarker polypeptides or RNA hybridization probes that can selectively bind mRNA biomarkers (or cDNA amplified therefrom), having specificity for one or more biomarkers disclosed herein. The probes can in some embodiments be bound to a substrate. Such a kit can comprise devices and reagents for the analysis of at least one test sample. The kit can further comprise instructions for using the kit and conducting the analysis. Optionally the kits can contain one or more reagents or devices for converting a marker level to a diagnosis or prognosis of the subject.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195, DNA Cloning, Volumes I and II, Glover, ed., 1985, Oligonucleotide Synthesis, M. J. Gait, ed., 1984, Nucleic Acid Hybridization, D. Hames & S. J. Higgins, eds., 1984; Transcription and Translation, B. D. Hames & S. J. Higgins, eds., 1984, Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

EXAMPLES

The following Examples have been included to illustrate modes of the presently-disclosed subject matter. In light of the present disclosure and the general level of skill in the art, those of skill will appreciate that the following Examples are intended to be exemplary only and that numerous changes, modifications, and alterations can be employed without departing from the scope of the presently-disclosed subject matter.

Example 1

Gastric Cancer Pathogenesis in Humans

Figure 2:
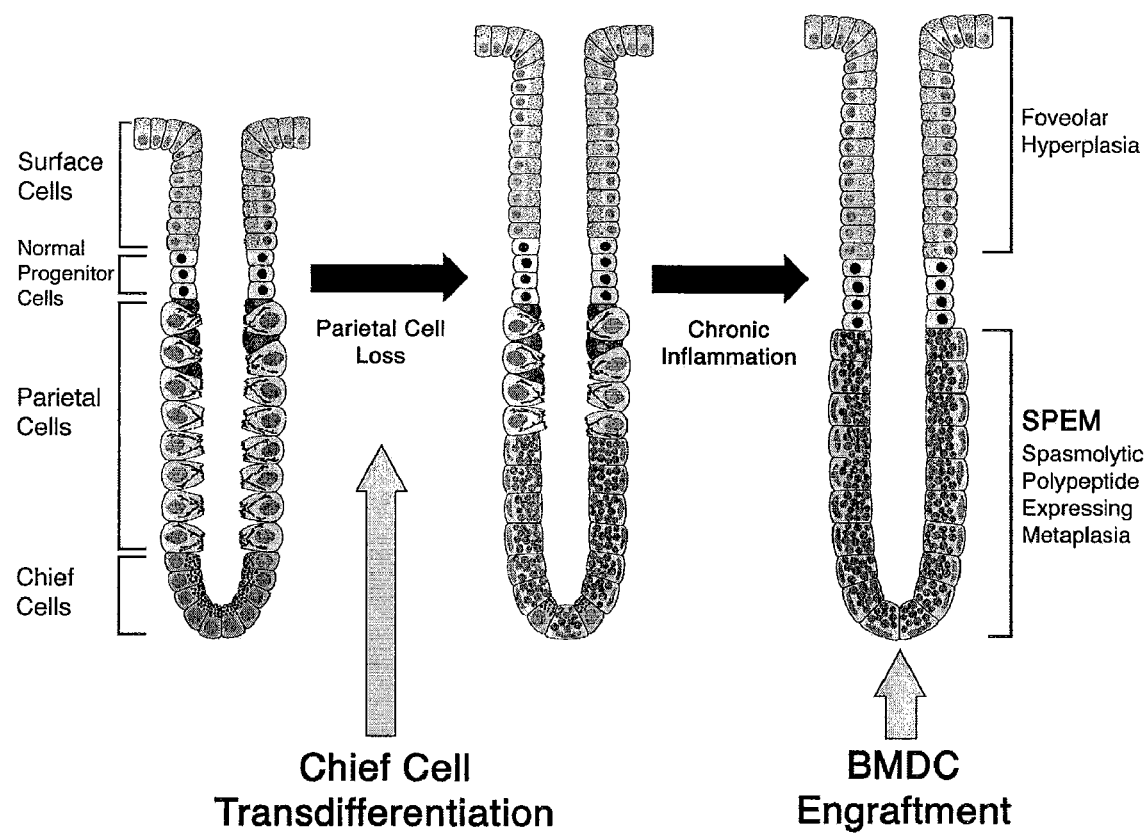
FIG. 2 depicts a scheme for the development of Spasmolytic Polypeptide-Expressing Metaplasia (SPEM) following oxyntic atrophy.

With reference to FIG. 2, most western authorities have traditionally considered goblet cell intestinal metaplasia as the leading candidate for origination of gastric cancer. See Correa. P. 1988. A human model of gastric carcinogenesis. *Cancer Res.* 48:3554-3560: Smith, V. C., Genta, R. M. 2000. Role of *Helicobacter pylori* gastritis in gastric atrophy, intestinal metaplasia, and gastric neoplasia. *Microsc Res Tech.* 48; 313-20; and Filipe, M. I., Munoz. N., Matko, I., Kato, I., Pome-Kim: V., Juersek, A., Teuchmann, S., Benz, M., Prijon, T. 1994. Intestinal metaplasia types and the risk of gastric cancer: a cohort study in Slovenia, *Int J Cancer.* 57; 324-329. Goblet cells are not found in the normal stomach, so the presence of cells with goblet cell morphology represents a clear metaplastic process with intestinal phenotype cells.

Nevertheless, little evidence exists linking directly intestinal metaplasia with dysplastic transformation. See Hattori, T. 1986. Development of adenocarcinomas in the stomach. *Cancer* 57:1528-1534. Indeed, intestinal metaplasia is not the only possible metaplastic precursor of cancer. A number of investigators, especially in Asia, have focused attention on the presence of metaplastic glands in the fundus with a general phenotype similar to that of the antral or pyloric glands. See Hattori, T. 1986. Development of adenocarcinomas in the stomach. *Cancer* 57:1528-1534. This phenotypic antralization of the fundus or pseudopyloric metaplasia is commonly associated with intestinal type adenocarcinoma. Referring again to FIG. 2, a similar metaplastic process has been described as Spasmolytic Polypeptide-Expressing Metaplasia or SPEM: which is characterized by the presence of trefoil factor 2 (TFF2 or spasmotytic polypeptide) immunoreactive cells in the gastric fundus with morphological characteristics similar to deep antral gland cells or Brunner's gland cells. See Schmidt, et al.

SPEM was associated with greater than 90% of resected gastric cancers in three studies in the United States, Japan and Iceland, See Schmidt, et al.; and Halldorsdottir, et al. Spasmotytic polypeptide expressing metaplasia (SPEM) associated with gastric cancer in Iceland. Dig.Dis.Sci. 48:431-441. In addition, similar findings were recently reported for subjects from Korea, and expression of TFF2 correlated with metastasis. See Dhar, D. K., Wang, T. C., Maruyama, R., Udagawa, J., Kubota, H., Fuji, T., Tachibana, M., Ono, T., Otani, H., and Nagasue. N. 2003. Expression of cytoplasmic TFF2 is a biomarker of tumor metastasis and negative prognostic factor in gastric cancer. *Lab Invest* 83:1343-1352. In all of these studies, SPEM was present as often or more often in association with cancer than goblet cell intestinal metaplasia. White TFF2 immunoreactivity was less prominent in advanced cancers, in the Iceland study, TFF2 immunoreactivity was observed in greater than 50% of early gastric cancers. See Halldorsdottir, et al. All of these studies in humans demonstrate the importance of SPEM and intestinal metaplasia as putative pre-neoplastic metaplasias in humans.

Example 2

Induction of SPEM Following Acute Oxyntic Atrophy

The orally active, cell permeant neutrophil elastase inhibitor, DMP-777, has allowed examination of SPEM induction following acute oxyntic atrophy in the absence of significant inflammatory infiltrate. Mice or rats treated with high doses of oral DMP-777 (>200 mg/kg/d) demonstrate a rapid loss of parietal cells with three days of administration. See Goldenring, J. R., Ray, G. S., Coffey, R. J., Meunier, P. C., Haley, P. J., Barnes, T. B., and Car, S. D. 2000. Reversible drug-induced oxyntic atrophy in rats. *Gastroenterology.* 18:1080-1093 ("Goldenring, et al."), and Nomura, S., Settle, S. H., Leys, C., Means, A. L., Peek, R. M., Jr., Leach, S. D., Wright, C. V. E., Coffey, R. J., and Goldenring, J. R. 2005. Evidence for repatterning of the gastric fundic epithelium associated with Menetrier's disease and TGFa overexpression. *Gastroenterology* 128:1292-1305 ("Nomura, et at. (2005)"). The acute oxyntic atrophy is followed immediately with prominent foveolar hyperplasia and then, after 7 to 10 days of oxyntic atrophy, SPEM develops in the fundus. These investigations have demonstrated that the induction of gastric metaplasia is a direct result of the loss of parietal cells. These results are compatible with the loss of prodifferentiative growth factors secreted by parietal cells, which could include the EGF receptor ligands TGF-α, amphiregulin, and HB-EGF as well as sonic hedgehog. In this model of acute oxyntic atrophy, gastrin seems to be the major driving force for foveolar hyperplasia, since gastrin knockout mice do not develop surface cell hyperplasia in response to DMP-777 treatment. See Nomura, et al. (2005). Nevertheless, the absence of gastrin appears to promote the development of SPEM, with rapid induction of metaplasia after only one day of DMP-777 treatment.

More recent studies have demonstrated that the reduction in EGF receptor signaling in wave-2 mice carrying a hypomorphic mutation, which reduces EGF receptor tyrosine kinase activity, also causes acceleration of SPEM development following DMP-777 treatment. See Ogawa, M., Nomura, S., Wang, T. C., and Goldenring, J. R. 2006. Altered metaplastic response of waved-2 EGF receptor mutant mice to acute oxyntic atrophy. *Am J Physiol* 290:G793-0804. These studies have demonstrated that intrinsic paracrine and endocrine regulators modulate the emergence of metaplasia following the loss of parietal cells. While the DMP-777 treatment model allows rapid induction of metaplasia, it should be noted that even after prolonged administration of drug for up to a year, no dysplastic lesions are ever observed in mice or rats despite the profound oxyntic atrophy and SPEM. These results appear to accrue from the absence of significant inflammatory infiltrate in DMP-777 treated animals. Without wishing to be bound by theory, the lack of infiltrate likely is a result from the major action of this drug as a cell-permeant inhibitor of neutrophil elastase. These studies have demonstrated that SPEM develops in response to the loss of parietal cells, even in the absence of inflammatory infiltrate. Moreover, these investigations point out that the presence of chronic inflammation is a requirement for development of dysplasia from metaplasia.

A key observation in these studies relates to the rapid induction of SPEM in response to DMP-777 treatment in gastrin knockout mice. Gastrin deficient mice develop SPEM after only one dose of DMP-777, compared to the 7-10 days required in wild type C57BL/6. See Nomura, et al.(2005). Classically, it has been believed that all fundic gastric lineages are derived from the progenitor cell zone located in the upper neck region of glands. Nevertheless, more recent studies in mice have indicated that chief cells develop from redifferentiation of mucous neck cells without going through an intermediated proliferating progenitor.

Whether this is a redifferentiation or a transdifferentiation, the findings indicate that classes of gastric cells can undergo alterations in their transcriptome as part of normal differentiation along the grand axis. While it was previously suggested that SPEM might develop from cryptic progenitor cells located at the bases of fundic glands, these results suggest that SPEM develops through transdifferentiation of chief cells. Indeed, the presence of cells at the base of glands expressing both intrinsic factor (a chief cell biomarker in mice) and TFF2 in separate granules has been found to be a good reflection of SPEM induction. Gastrin-deficient mice treated with DMP-777 have a rapid increase in dual expressing cells after only one day of treatment. In addition to dual expressing cells, the presence of BrdU-labeled S-phase cells at the bases of fundic glands, distinct from the normal progenitor zone located near the lumen, has been observed. See Goldenring, et al., and Nomura, et al.

While the proliferative rate observed in DMP-777-treated mice is considerably lower than that in SPEM in *H. felis*-infected mice, the rapid induction of basally-located proliferating cells suggests that some transdifferentiating cells can repenter the cell cycle. Thus, SPEM cells may eventually become self-renewing or be influenced by inflammatory regulators towards metaplastic expansion or dysplastic transformation.

Example 3

Gene Microarray Analysis of Chief Cell Transdifferentiation

A mouse model of acute oxyntic atrophy was used to study the earliest events following loss of parietal cells. Treatment of rodents with the parietal cell protonophore DMP-777 causes rapid loss of acid-secreting parietal cells within one to three days. In wild-type C57BL/6 mice, loss of parietal cells is followed by the emergence of SPEM in the deep fundic glands after 10-14 days of drug treatment coincident with the appearance of BrdU-labeled proliferating cells also at the bases of fundic glands. See Nomura, S. Yamaguchi, H. Wang, T. C., Lee, J. R., and Goldenring, J. R. 2004. Alterations in gastric mucosal lineages induced by acute oxyntic atrophy in wild type and gastrin deficient mice. *Amer. J. Physiol.* 288: G362-G375. At the very bases of these metaplastic glands, the presence of cells dually immunoreactive for both TFF2 and intrinsic factor (a chief cell specific biomarker in rodents) was observed. See Ogawa, M., Nomura, S., Wang, T. C., and Goldenring, J. R. 2006. Altered metaplastic response of waved-2 EGF receptor mutant mice to acute oxyntic atrophy. *Am J Physiol* 290:G793-G804; Nomura, S., Baxter, S., Yamaguchi, T., Leys, C., Vartapetian, A. B., Fox, J. G., Lee, J. R., Wang, T. C., and Goldenring, J. R. 2004. Relationship of spasmolytic polypeptide expressing metaplasia (SPEM) to pre-neoplasia in *H. felis*-infected mice. *Gastroenterology* 127:582-594; and Yamaguchi, H., Goldenring, J. R., Kaminishi, M., and Lee, J. R. 2002. Association of spasmolytic polypeptide expressing metaplasia (SPEM) with carcinogen administration and oxyntic atrophy in rats. *Lab. Invest.* 82:1045-1052.

More recently it was found that gastrin knockout mice develop SPEM after only a single dose of DMP-777 again associated with the presence of BrdU positive S-phase cells at the bottoms of gastric glands. See Nomura, S., Yamaguchi, H., Wang, T. C., Lee, J. R., and Goldenring, J. R. 2004. Alterations in gastric mucosal lineages induced by acute oxyntic atrophy in wild type and gastrin deficient mice. Amer. J. Physiol. 288:G362-G375. These results, along with the identification of dually immunoreactive cells, has led to the hypothesis that SPEM arises initially from transdifferentiation of chief cells. To examine this hypothesis more directly, chief cells were microdissected from the very bases of untreated gastrin knockout mice as well as SPEM cells at the base of fundic glands after 1 and 3 days of treatment with DMP-777. Total RNA was prepared from 10,000 cells isolated from 4 different mice in each group. For each of the 12 samples, linear amplification was performed and Affymetrix Mouse 2.0 gene microarrays were probed. The data were then analyzed to determine genes whose expression was up-regulated or down-regulated at least 2 fold. The results provided the following findings. First, there were not any pro-apoptotic genes detected in the cohort of up-regulated transcripts. Second, 30 genes were identified as being involved in G1-S interface transition, including 5 MCM proteins, BRCA1, RIS2, RAD51, TACC3 and ligase1. Immunocytochemistry was used to confirm the upregulation of MCM3 as well as TACC3 in SPEM cells located at the base of fundic glands in mice treated for 1 or 3 days with DMP-777. All of these changes are consistent with alterations moving towards a proliferative phenotype. While it was previously noted that treatment of gastrin KO mice with DMP-777 causes an increase in BrdU-labeled cells at the bases of fundic glands, the increase in labeling does not appear to account for the emergence of the SPEM phenotype. See Nomura, S., Yamaguchi, H., Wang, T. C., Lee, J. R., and Goldenring, J. R. 2004. Alterations in gastric mucosal lineages induced by acute oxyntic atrophy in wild type and gastrin deficient mice. *Amer. J. Physiol.* 288:G362-G375. Thus the up-regulation of proteins involved in the G1/S interface is also consistent with transdifferentiation of chief cells into SPEM, since such changes would require a global transcriptome, alterations that would require unwinding of DNA and changes in gene activation including alteration in DNA methylation.

In addition to the biomarkers that indicate that transdifferentiation is occurring, the upregulated list contains several important putative biomarkers, which are either secreted proteins or cell surface proteins (Fold increases indicated as the exponential of 2), as shown in Table 2

TABLE 2

| Gene Name | | Day 1 Fold increase, Relative to Control | Day 3 Fold Increase, Relative to Control |
| --- | --- | --- | --- |
| LGALS3 | lectin, galactose binding, soluble 3 | 5.5 | 7.3 |
| IL1RN | interleukin 1 receptor antagonist | 4.7 | 4.2 |
| TR1P13 | thyroid hormone receptor interactor 13 | 3.5 | 3.0 |
| FIGNL1 | fidgetin-like 1 | 3.3 | 2.7 |
| CRIP1 | cysteine-rich protein 1, intestinal | 3.2 | 5.4 |
| S100A4 | S100 calcium-binding protein A4 | 2.8 | 2.5 |
| EXOSC8 | exosome component 8 | 2.6 | 2.8 |
| EXPI | extracellular proteinase inhibitor | 2.4 | 8.4 |
| BRRN1 | barren homolog, *Drosophila* | 2.2 | 3.1 |
| NELF | nasal embryonic LHRH factor | 2.1 | 3.7 |
| EREG | Epiregulin | 1.8 | 4.8 |
| TMEM40 | transmembrane protein 40 | 1.4 | 6.9 |
| TMEM109 | transmembrane protein 109 | 2.5 | 3.6 |

These proteins represent a cohort of proteins whose expression is increased significantly during transdifferentiation of chief cells to SPEM after oxyntic atrophy. As such these proteins can be biomarkers for gastric preneoplastic metaplasias.

In addition to those biomarkers set forth above in Table 2 among the up-regulated genes is human epididymis protein 4 (HE4). See Bingle, L., Singleton, V., and Bingle, C. D. 2002. The putative ovarian tumor biomarker gene HE4 (WFDC2), is expressed in normal tissues and undergoes complex alternative splicing to yield multiple protein isoforms. *Oncogene* 21:2768-2773; Bouchard, D., Morisset, D., Bourbonnais, Y., and Tremblay, G. M. 2006. Proteins with whey-acidic-protein motifs and cancer. *Lancet Oncol* 7:167-174; Galgano, M. T., Hampton, G. M., and Frierson, H. F. 2006. Comprehensive analysis of HE4 expression in normal and malignant human tissues. *Mod Pathol* 19:847-853; Hellstrom, I., Raycraft, J., Hayden-Ledbetter, M., Ledbetter J. A., Schummer, M., McIntosh, M., Drescher, C., Urban, N., and Hellstrom, K. E. 2003. The HE4 (WFDC2) protein is a biomarker for ovarian carcinoma. *Cancer Res* 63:3695-3700. Indeed, there was a greater than 16-fold increase in the expression of the HE4 gene that was observed. HE4 has been identified as a useful biomarker for certain cancers, such as ovarian cancer. See e.g., U.S. Patent Application Publication No. 2003/0108965. However, it was unexpected to identify HE4 as a useful biomarker for gastric cancer because it was believed that HE4 was not expressed in the stomach. See Galgano, M. T., Hampton, G. M.; and Frierson Jr., H. F. 2006. Comprehensive analysis of HE4 expression in normal and malignant human tissues. *Mod. Pathology.* 19: 847-853.

Figure 3:
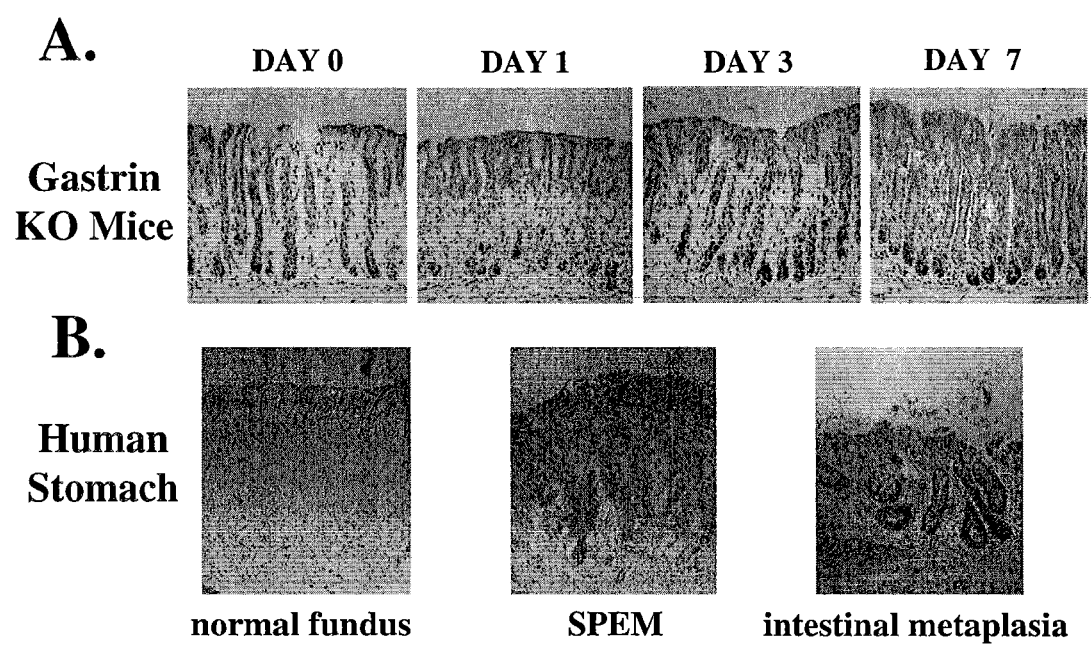
FIGS. 3A and 3B are a series of photomicrographs.

With reference to FIG. 3, little or no HE4 immunoreactivity was observed in the fundic mucosa of untreated mice. However, HE4 immunoreactivity was markedly increased in SPEM after only one day of treatment. Additionally, while the normal human fundus does not express HE4, it was found that both SPEM and intestinal metaplasia strongly express HE4.

Materials and Methods for Examples 4-8

Gene Microarray Analysis

Gastrin-deficient mice were constructed by targeted disruption of the gastrin gene and were maintained on a C57BL/6 background (Nomura S, Yamaguchi H, Wang T C, Lee J R, Goldenring J R. Alterations in gastric mucosal lineages induced by acute oxyntic atrophy in wild type and gastrin deficient mice. Amer.J.Physiol. 2004; In Press). Mice were treated for 1 or 3 days with oral gavage administration of DMP-777 (a gift of DuPont Pharmaceuticals), formulated in 0.5% methylcellulose (administered orally as a gavage once daily at 350 mg/kg/day). Untreated mice were utilized as controls. Mice were sacrificed and their stomachs were excised and opened along the greater curvature and processed for frozen sections for laser capture microdissection. From the untreated Gastrin-deficient mice, chief cells were microdissected from the bases of gastric glands. The emerging SPEM cells were microdissected from the bases of fundic glands of DMP-777-treated Gastrin-deficient mice after 1 or 3 days of oral drug administration. Cell collections (10,000 cells) and extractions of total RNA were performed as previously described (Nomura S, Baxter S, Yamaguchi T, Leys C, Vartapetian A B, Fox J G, Lee J R, Wang T C, Goldenring J R. Relationship of spasmolytic polypeptide expressing metaplasia (SPEM) to pre-neoplasia in *H. felis*-infected mice. Gastroenterology 2004; 127:582-594).

Total RNA from microdissected cells were reverse transcribed and amplified through two rounds of linear amplification using a Nugen Ovation kit to amplify and label 10-20 ng of RNA. The resulting single-strand cDNA product was purified by binding to and elution from a Qiagen QIAQUICK® column. The cDNA product was then quantitated and 2.2 μg of the fragmented, labeled product was hybridized to Affymetrix Mouse 430 2.0 microarrays overnight, with staining and scanning performed the next day. Gene expression was analyzed among microdissected cells from 4 untreated gastrin-deficient mice 4 mice treated with DMP-777 for one day and 4 mice treated with DMP-777 for three days. The raw gene expression data (.cel files) were converted to expression values using the Affy function in R (see the Bioconductor website). The expression levels between groups were compared first using an overall permutation F-test for difference between the groups (control, one day treatment and three days of treatment) using analysis of variance; if a statistically significant overall difference was seen then pair-wise differences between control and one day of treatment and control and three days of treatment were performed using permutation t-tests. We then further reduced the candidate probe list by requiring at least 4-fold differences between treated groups (day 1 and day 3) and control in those that showed a statistically significant pair-wise difference. All expression data analysis was performed using the SAFE package in R. Annotation and pathways were interrogated using the WebGestalt software (Zhang B, Kirov S, Snoddy J. WebGestalt; an integrated system for exploring gene sets in various biological contexts. Nucleic Acids Res 2005; 33:W741-8).

Quantitative Polymerase Chain Reaction

Total RNA isolated from laser-capture microdissected cell collections from the stomachs of normal and DMP-777 1-day-treated and DMP-777 3-day—treated gastrin-deficient mice was analyzed by quantitative PCR assays. Reverse transcription from each total RNA sample was performed using random primers and Quantiscript Reverse transcriptase (Qiagen. Valencia, Calif.), for 30 minutes at 42° C. Quantitative real-time PCR was performed with a 3-step method using the Bio-Rad iCycler iQ real-time PCR detection system (Bio-Rad Laboratories, Hercules, Calif.). Each reaction was carried out in a 50 µL mixture consisting of QuantiTect SYBR Green PCO Master Mix (Qiagen), and 1 µL of template cDNA. The sequences of the primers used are listed in Table 3. The PCR conditions for quantitative real-time PCR were; 95° C. for 10 minutes 45 cycles of 94° C. for 15 seconds, 60° C. for 30 seconds, and 72° C. for 30 seconds. Quantitation of cDNA template in each sample was determined using the comparative threshold cycle ($C_T$) method using GAPDH as a control, as described previously (Nomura S, Baxter S, Yamaguchi T, Leys C, Vartapetian A B, Fox J G, Lee J R, Wang T C, Goldenring J R. Relationship of spasmolytic polypeptide expressing metaplasia (SPEM) to pre-neoplasia in *H. felis*-infected mice. Gastroenterology 2004; 127:582-594). Statistical comparisons of the mean $\Delta\Delta C_T$ between groups were determined using the Mann-Whitney U Test

TABLE 3

Primer Sets Used For Quantitative PCR

Artificially-generated PCR sense primer sequence specific for GAPDH
Artificially-generated PCR antisense primer sequence specific for GAPDH

| | | |
|---|---|---|
| GAPDH | Sense 5'-TGA CGT GCC GCC TGG AGA AA-3' | (SEQ ID NO: 1) |
| | Antisense 5'-CCG GCA TCG AAG GTG GAA GAG-3' | (SEQ ID NO: 2) |
| | Product size: 160 bp | |
| MCM3 | Sense 5'-GCG CAG AGA GAC TAC TTG GAC-3' | (SEQ ID NO: 3) |
| | Antisense 5'-TGC TTG GCG TAG GTG G-3' | (SEQ ID NO: 4) |
| | Product size: 239 bp | |
| MCM5 | Sense 5'-GCG GCA TTA CAA CCT GGG TGA-3' | (SEQ ID NO: 5) |
| | Antisense 5'-ACG GGC TGG CAT CTG ACT TGA-3' | (SEQ ID NO: 5) |
| | Product size 224 bp | |
| MCM7 | Sense 5'-CAC GCT CAA TGC CCG ATG CT-3' | (SEQ ID NO: 7) |
| | Antisense 5'-TTG TCT CTG TCG GGC CGG TCT-3' | (SEQ ID NO: 8) |
| | Product size: 159 bp | |
| ST3GAL6 | Sense 5'-CAT ATA TCA CCA GCG AAG CAG-3' | (SEQ ID NO: 9) |
| | Antisense 5'-TGG CAT TCC CGT AGT AGT GT-3' | (SEQ ID NO: 10) |
| | Product size: 198 bp | |
| ATF3 | Sense 5'-GAT GCA ACG CGC TCC CAG-3' | (SEQ ID NO: 11) |
| | Antisense 5'-GGC GGC CAG GGT CCA GAG AAC-3' | (SEQ ID NO: 12) |
| | Product size 163 bp | |
| HE4 | Sense 5'-TGC CTG CCT GTC GCC TCT G-3' | (SEQ ID NO: 13) |
| | Antisense 5'-TGT CCG CAC AGT CCT TGT CCA-3' | (SEQ ID NO: 14) |
| | Product size: 171 bp | |
| IL1RN | Sense 5'-TTG GCC TAG GTG TCT TCT GCT-3' | (SEQ ID NO: 15) |
| | Antisense 5'-TAT GTG ATG CCC TGG TGG TT-3' | (SEQ ID NO: 16) |
| | Product size: 243 bp | |
| TFF2 | Sense 5'-TGC TTT GAT CTT GGA TGC TG-3' | (SEQ ID NO: 17) |
| | Antisense 5'-GGA AAA GCA GCA GTT TCG AC-3' | (SEQ ID NO: 18) |
| | Product size: 191 bp | |

Immunohistochemistry

Excised stomachs from Gastrin-deficient mice treated with DMP-777 or untreated controls embedded in paraffin were used for immunohistochemistry analysis Stomachs from C57BL/6 wild-type mice and sections from *H. felis*-infected C57BL/6 mice (infected for 6 months) were also examined with staining as a comparison. For immunohistochemistry, except for Mist1 staining, deparaffinized sections were pre-treated with antigen retrieval using Target Retrieval solution (DakoCytomation, Glostrup, Denmark) at 120° C. for 15 minutes, followed by immediate cooling using iced water. For immunohistochemistry of Mist1, Trilogy antigen retrieval solution (Cell Marque, Austin. Tex.) was used during the antigen retrieval procedure. Sections were treated with 2% blocking serum and then incubated with the primary antibody overnight at 4° C. Immunostaining was performed with the following primary antibodies; murine monoclonal immunoglobulin M (IgM) anti-trefoil factor family 2 (TFF2, a gift from Sir Nicholas Wright, Cancer Research UK; 1:1000); rabbit anti-Mist1 (1:2000); murine monoclonal anti-H/K-ATPase (a gift from Dr. Adam J. Smolka, Medical University of South Carolina; 1:100,000); rabbit anti-HE4 (1:2000); rabbit anti-intrinsic factor (a gift from Dr. David Alpers, Washington University, St. Louis; 1:2000);, goat anti-Intrinsic factor (1:2000): rabbit anti-MCM3 (1:2000); rat monoclonal anti-Ki67 (TEC-3, DakoCytomation; 1:200).

For immunofluorescence analysis, Cy3-goat anti-mouse IgM antibody, Cy5-goat anti-mouse IgG antibody (Jackson ImmunoResearch, West Grove, Pa.) and Alexa488 goat anti-rabbit IgG (Invitrogen, Carlsbad, Calif.) were used. PRO-LONG® Gold Antifade Reagent with DAPI (Invitrogen) was used for nuclear counterstain and mounting medium.

For immunohistochemistry with detection with diaminobenzidine, the sections were incubated with biotinylated secondary antibody followed by horseradish peroxidase-conjugated streptavidin. Chromogen was developed with diaminobenzidine (Biogenex, San Ramon, Calif.). For immunohistochemistry with alkaline-phosphatase detection, the sections were incubated with biotinylated secondary antibody followed by alkaline-phosphatase-conjugated avidin-biotin complex. Chromogen was developed with VECTOR® Red Substrate (Vector Laboratories, Burlingame, Calif.). All sections were counterstained with Gill's hematoxylin.

Sections were viewed and photographed on Zeiss AXIO-PHOT® microscope equipped with an AXIOVISION® digital imaging system (Zeiss) or FLUOVIEW® FV1000 confocal microscope system (Olympus).

Two tissue arrays were utilized for staining of human stomach samples as previously described (Leys C M, Nomura S, Rudzinski E, Kaminishi M, Montgomery E, Washington M K, Goldenring J R. Expression of Pdx-1 in human gastric metaplasia and gastric adenocarcinoma. Hum Pathol 2006; 37:1162-8). One tissue array contained samples of normal gastric mucosa and examples of SPEM and intestinal metaplasia from 33 gastric resections at the University of Tokyo, Japan. The second array contained normal mucosa and gastric adenocarcinomas from 44 subjects resected at Vanderbilt University, Nashville, Tenn.

Electron Microscopy Analysis

Fresh specimens from the gastric fundic region of untreated controls and 3-day DMP-777 treated gastrin-deficient mice fixed for 2.5 hour on ice in 2.5% glutaraldehyde, 0.1 M Cacodytate Buffer in PBS. The samples were fixed overnight at 4° C. in 1% osmium tetroxide ($OSO_4$) and 0.1M Cacodylate Buffer. Subsequently, the samples were subjected to an ethanol dehydration series and embedded in Spurrs resin. 50~100 nm thin sections were cut and collected on 200-mesh, formvar-coated copper grids. After drying overnight, the grids were contrast stained with 2% depleted Uranyl Acetate (UA) and then stained with saturated lead citrate. Samples were examined on a Philips CM12 Electron Microscope.

Example 4

Morphological Evidence for Transdifferentation

Figure 4:
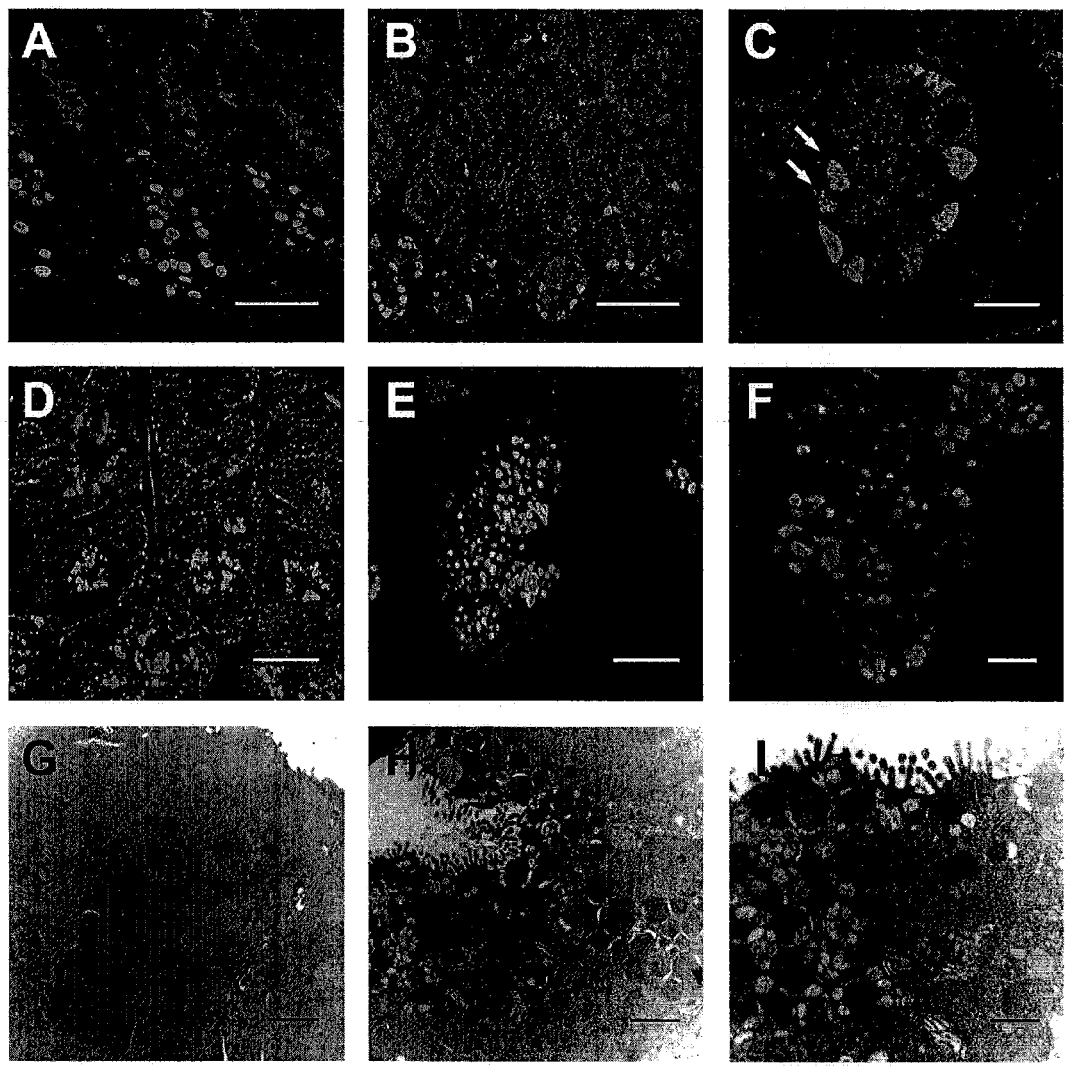
FIGS. 4A-4I are a series of photomicrographs showing the characterization of emerging SPEM.

Given results suggesting the rapid evolution of SPEM in gastrin-deficient mice (Nomura S, Yamaguchi H, Wang T C, Lee J R, Goldenring J R. Alterations in gastric mucosal lineages induced by acute oxyntic atrophy in wild type and gastrin deficient mice. Amer.J.Physiol. 2004), it was evaluated whether mature chief cells expressing the bHLH transcription factor Mist1 could give rise to SPEM in DMP-777-treated mice (Ramsey V G, Doherty J M, Chen C C, Stappenbeck T S, Konieczny S F, Mills J C. The maturation of mucus-secreting gastric epithelial progenitors into digestive-enzyme secreting zymogenic cells requires Mist1. Development 2007; 134:211-22). In untreated gastrin-deficient mice, the nuclei of mature chief cells stained with antibodies against Mist1, and mucous neck cells stained with TFF2 antibodies (FIG. 4A). In contrast, in mice treated with DMP-777 for three days, the number of Mist1 immunoreactive cells decreased at the bases of glands, and a number of the Mist1 positive cells were dual immunoreactive for TFF2 (FIG. 4, B-C). In the normal stomach, TFF2 and intrinsic factor were expressed in secretory granules of either mucous neck cells or chief cells, respectively (FIG. 4D). However, in gastrin deficient mice treated for 3 days with DMP-777, SPEM cells expressing two separate populations of TFF2 and intrinsic factor staining granules were present at the bases of fundic glands (FIG. 4, E-F). These results suggested that the loss of parietal cells in DMP-777-treated mice induced a marked alteration in the cellular phenotype of chief cells.

To examine cell lineages more precisely, the chief cells from untreated gastrin-deficient mice and emerging SPEM cells from gastrin-deficient mice treated for 3 days with DMP-777 were examined by electron microscopy (FIG. 4, G-I). In untreated animals, normal chief cells were observed with uniformly staining zymogen granules (FIG. 4G). However, in the DMP-777-treated cells, a heterogeneous set of granule morphologies was observed in SPEM cells at the bases of fundic glands (FIG. 4, H-I). The SPEM cells did contain some normal appearing zymogen granules, generally in the perinuclear region, but they also showed large granules with electron dense material and single electron lucent circular peripheral inclusions, a morphology more consistent with mucous secretory granules. In addition, numerous smaller electron lucent granules were observed in the sub-luminal region. These changes in chief cell granule morphologies were observed with no morphological evidence of apoptosis. These results indicated that chief cells were altering their granule contents to adopt morphologies more similar to mucous secreting cells (Ramsey V G Doherty J M, Chen C C, Stappenbeck T S, Konieczny S F, Mills J C. The maturation of mucus-secreting gastric epithelial progenitors into digestive-enzyme secreting zymogenic cells requires Mist1. Development 2007; 134:211-22).

Example 5

Gene Microarray Analysis of the Emergence of SPEM

To analyze alterations in gene expression attendant with the emergence of SPEM, laser capture microdissection was utilized to isolate chief cells from untreated gastrin-deficient mice as well as the emerging SPEM cells from mice treated with DMP-777 for either one or three days. Affymetrix gene microarrays were probed with the mRNAs prepared from microdissected cells. Table 4 demonstrates that DMP-777-treatment led to the rapid up-regulation of a number of transcripts after only one dose of drug. Pathway analysis showed that the most prominent sets of transcripts were involved in cell cycle regulation and nucleotide metabolism (Table 4A). In particular, 34 out of the top 50 probes for up-regulated transcripts detected messages for proteins implicated in the regulation of the G1/S transition including 5 MCM proteins, ATF3, RIS2, RAD51, TACC3 and ligase1. No pro-apoptotic genes were detected in the cohort of up-regulated gene transcripts in both 1 and 3 days of DMP-777-treatment. No clear pattern of gene transcript down-regulation was observed, although it is notable that there was a significant decrease in transcripts for lipase, a chief cell product. In addition to the up-regulation of G1/S modulators, we also observed the prominent up-regulation of the expression for a number of secreted regulators including two WAP domain proteins, WFDC2 (HE4) and WDNM1 (Expi), Interleukin-1 receptor antagonist (IL1RN) and Epiregulin (Table 4B).

TABLE 4

| Gene Symbol | 1 DAY DMP-777 vs CONTROL | 3 DAYS DMP-777 vs CONTROL |
|---|---|---|
| A. Up-regulated Transcripts Associated with Cell Cycle | | |
| Atf3 | 311.4 | 10.1 |
| Uhrf1 | 35.3 | 8.8 |
| Cenph | 25.7 | 10.7 |
| Mcm6 | 25.1 | 36.4 |
| Ris2* | 21.5 | 41.3 |
| Mcm5 * | 18.1 | 36.2 |
| Cdca5 | 17.3 | 36.1 |
| Mcm5 * | 13.9 | 18.2 |
| Rad51 | 13.5 | 10.5 |
| Rad51ap1 * | 12.9 | 6.1 |
| Mcm10 * | 12.2 | 38.3 |
| Cdc2a | 11.7 | 7.0 |
| Tk1 | 10.1 | 11.5 |
| Clspn | 9.5 | 8.5 |
| Lig1 | 9.3 | 9.6 |
| Cdca1 | 9.2 | 8.1 |
| 5sscal | 8.9 | 12.3 |
| Dcc1 | 8.8 | 10.0 |
| Rad51ap1 * | 8.7 | 7.4 |
| Gadd45b | 8.6 | 5.0 |
| Rfc4 | 8.5 | 8.4 |
| Rrm1 | 8.4 | 8.4 |
| Rfc3 | 8.1 | 6.1 |
| Pole | 7.5 | 11.3 |
| Ncapg | 7.5 | 3.2 |
| Prc1 | 7.5 | 6.9 |
| Top2a | 7.3 | 6.4 |
| Cdca5 | 7.3 | 8.7 |
| Ris2* | 7.3 | 10.3 |
| Prc1 | 7.0 | 7.4 |
| Mcm10 * | 6.7 | 10.1 |
| Rad54b | 6.7 | 6.6 |
| B. Up-regulated transcripts for soluble regulators | | |
| Lgals3 | 46.8 | 153.3 |
| Il1rn | 25.4 | 18.5 |
| Trip13 | 10.3 | 8.6 |
| Fignl1 | 10.2 | 6.6 |
| Crip1 | 9.5 | 42.6 |
| Wfdc2 | 8.9 | 67.5 |
| ExoscB | 6.2 | 6.7 |
| WDNM1 | 5.2 | 345.9 |
| Ereg | 3.6 | 28.9 |

Example 6

Quantitative PCR Analysis of the Emergence of SPEM

Figure 5:
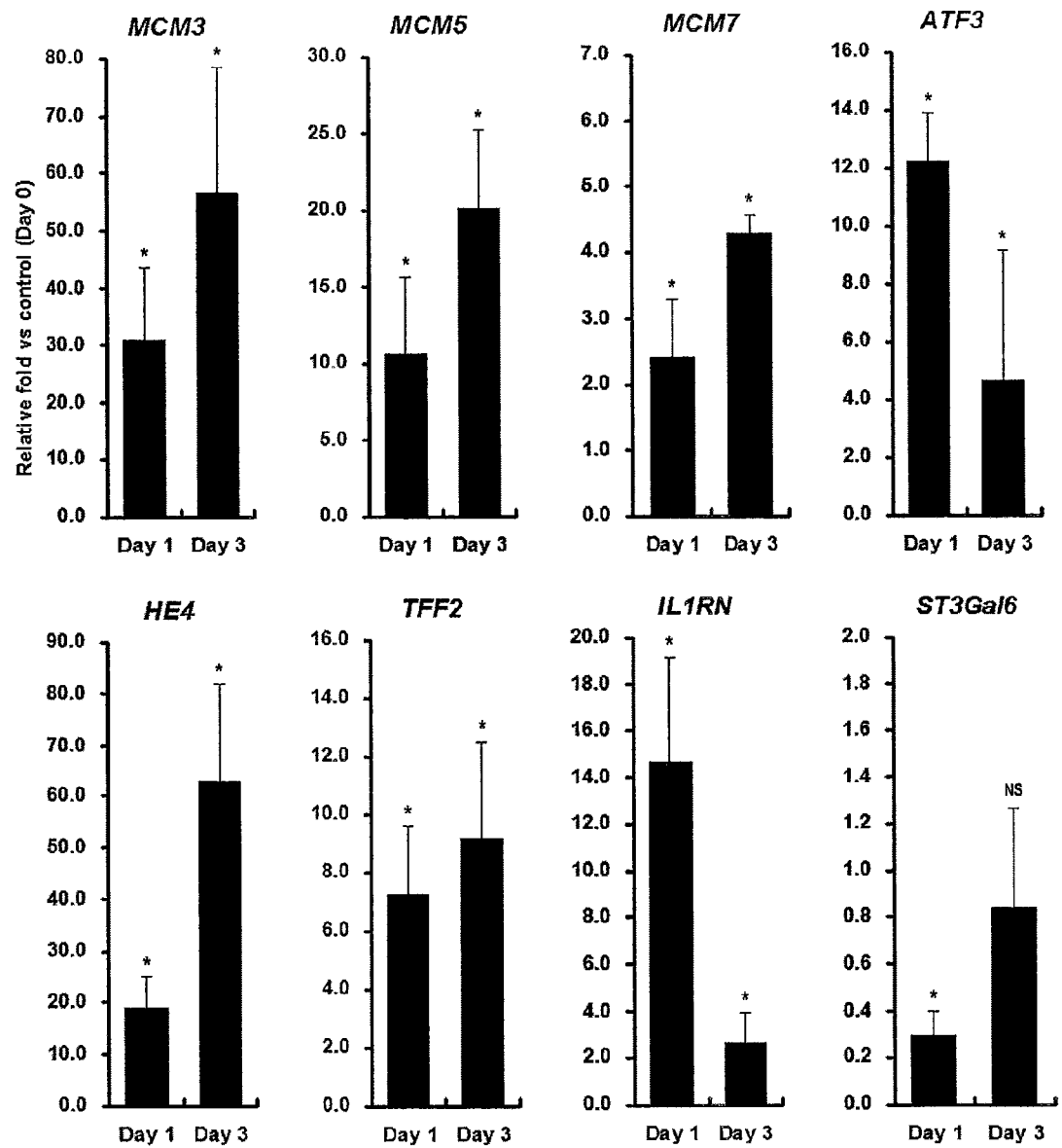
FIG. 5 is a series of graphs showing results from quantitative PCR analysis of transcripts during the emergence of SPEM. Expression of selected up-regulated or down-regulated transcripts in microdissected lineages was examined using quantitative PCR to validate the results of the gene microarray studies. Results are represented as fold change in expression compared with levels in untreated chief cells (n=3, +/− standard error of the mean, SE). *$p<0.05$ by Mann-Whitney U.

To validate the results of the gene microarray studies, the expression of selected up-regulated or down-regulated transcripts in microdissected lineages was evaluated using quantitative PCR. The up-regulation of G1/associated transcripts was confirmed, including MCM3, MCM5, MCM7 and ATF3 (FIG. 5). The up-regulation of transcripts for putative soluble mediators was also confirmed, including HE4 and IL1RN and the down-regulation ST3Gal6 was confirmed. It has been previously noted that Affymetrix gene arrays do not detect accurately changes in TFF2 expression (Nomura S, Baxter S, Yamaguchi T, Leys C, Vartapetian A B, Fox J G, Lee J R, Wang T C, Goldenring J R. Relationship of spasmolytic polypeptide expressing metaplasia (SPEM) to pre-neoplasia in *H. felis*-infected mice. Gastroenterology 2004; 127:582-594). However, by quantitative PCR assays, TFF2 levels were elevated greater than 7-fold in emerging SPEM from DMP-777 treated animals (FIG. 5).

Example 7

MCM3 and TACC3 Expression is Increased Following Acute Oxyntic Atrophy

Figure 6:
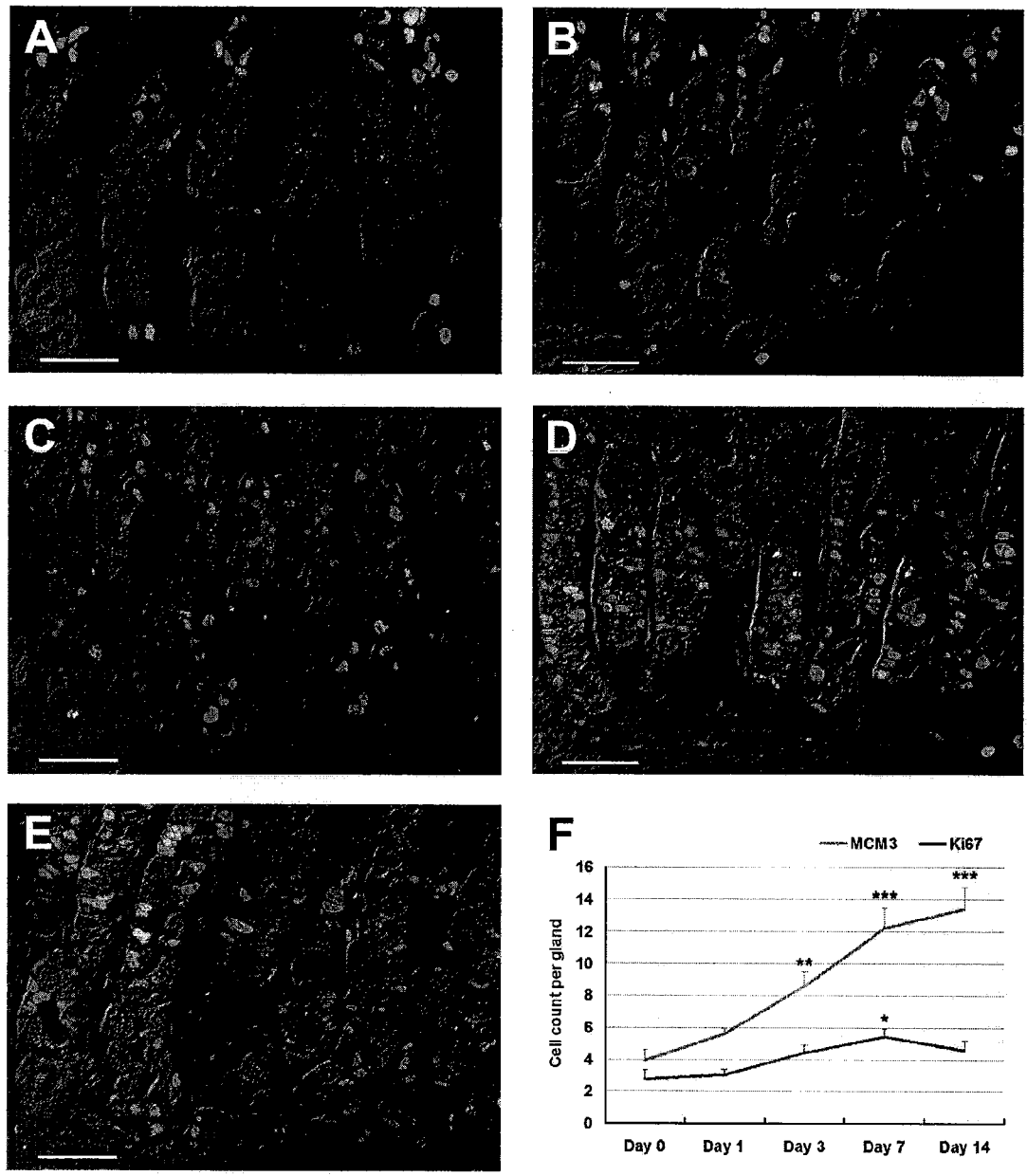
FIGS. 6A-6E are photomicrographs and FIG. 6F is a graph showing results of MCM3 expression during acute oxyntic atrophy. Sections from an untreated mouse (FIG. 6A) or mice treated with DMP-777 for 1 (FIG. 6B), 3 (FIG. 6C), 7 (FIG. 6D) or 14 (FIG. 6E) days were dual stained with antibodies against MCM3 (green, light staining in gray scale photo) and antibodies against Ki67 (red, dark staining in gray scale photo). With increasing amounts of treatment DMP-777, an increase in MCM3 staining in cells at the bases of glands (Scale bar: 40 μm) was observed.

To investigate the up-regulation of transcripts involved in G1/S transition, the stomachs of DMP-777-treated or untreated gastrin-deficient mice were examined with dual-staining with antibodies against MCM3 and Ki67, a general biomarker of proliferating cells (FIG. 6). In untreated mice, MCM3 was predominantly localized to cells within the normal progenitor zone located in the neck region of the glands (FIG. 6A). Nevertheless, occasionally nuclear MCM3 staining in cells at the bases of fundic glands was observed (FIG. 6A). In DMP-777 treated mice, in addition to MCM3 staining in the proliferative neck region, prominent nuclear staining in SPEM cells at the bases of the fundic glands was also observed (FIG. 6, B-E). MCM3 expressing cells were more widely distributed within SPEM cells compared to Ki67 labeled cells. While Ki67 positive cell numbers showed only a small increase after DMP-777 treatment, the number of MCM3 positive cells increased after 1 day of DMP-777 (FIG. 6B) treatment and remained elevated through 14 days of treatment (FIG. 6, C-E). The results suggest that MCM3 activation in emerging SPEM is more prominent than active entry into the cell cycle (FIG. 6F).

Figure 7:
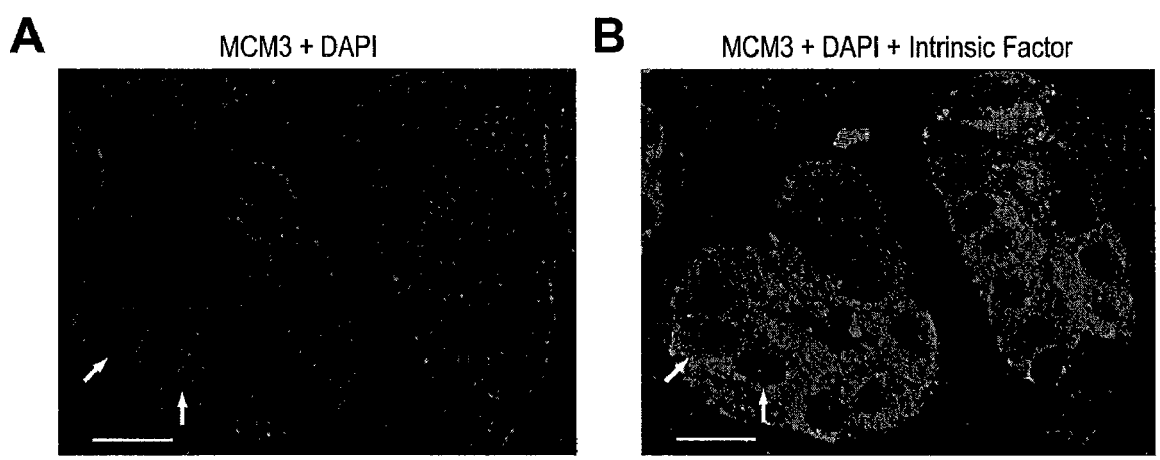

While these results indicated that SPEM cells emerging from the bases of gastric glands expressed MCM3, it was also sought to understand the identity of MCM3 staining cells at the bases of glands in untreated mice. The observation was not specific to gastrin deficient mice, since similar MCM3-expressing cells were observed at the bases of glands in wild type C57BL6 mice (data not shown). Dual staining of sections for both MCM3 and intrinsic factor, a biomarker of mature chief cells, was therefore performed (FIG. 7). In all cases, cells with MCM3 staining nuclei at the bases of glands were also immunoreactive for intrinsic factor, indicative of chief cells (FIG. 7B).

Figure 8:
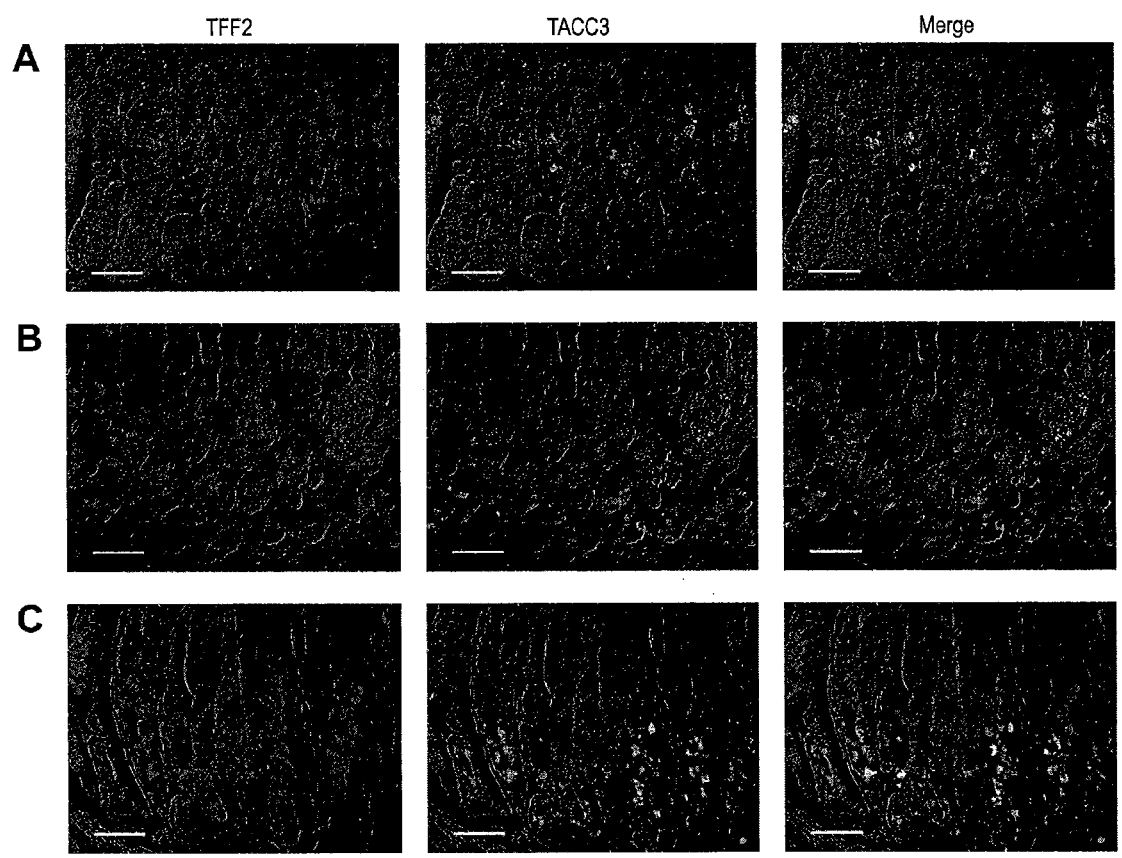
FIGS. 8A-8C are photomicrographs showing immunohistochemical staining for TACC3 in untreated and DMP-777 treated gastrin-deficient mice. Sections of fundic mucosa from untreated gastrin deficient mice (8A) and mice treated with DMP-777 for either 1 day (8B) or 3 days (8C) were dual stained for TFF2 and TACC3. Dual color overlay images are shown at the far right (Merge). After only one day of DMP-777 treatment the TACC3 expression was evident in cells at the bases of gastric glands and TACC3 expression increased in these cells following treatment with DMP-777 for 3 days.

The expression of TACC3, a protein associated with the initiation of cell cycle (Aitola M, Sadek C M, Gustafsson J A, Pelto-Huikko M, Aint/Tacc3 is highly expressed in proliferating mouse tissues during development, spermatogenesis, and oogenesis. J Histochem Cytochem 2003; 551:455-69), was also examined in DMP-777-treated mouse stomachs. While little TACC3 expression was noted in the stomachs of untreated mice (FIG. 5), TACC3 expression was strongly up-regulated in SPEM cells at the bases of fundic glands following treatment with DMP-777 for 3 days (FIG. 8).

Example 8

Up-Regulation of HE4 in Gastric Metaplasia and Cancer

As noted above, emergence of SPEM also coincided with up-regulation of several secreted factors. Immunostaining for the WAP domain protein HE4 in gastrin-deficient mice was therefore performed. Immunostaining showed little detectable HE4 in the normal gastric mucosa of gastrin-deficient (FIG. 9A) or wild-type C57BL6 mice. Nevertheless, in DMP-777 treated mice, a prominent up-regulation of HE4 expression in SPEM cells at the bases of fundic glands was observed (FIG. 9B). In immunofluorescence studies, HE4 granules stained distinctly from TFF2 staining granules in SPEM cells. To evaluate whether HE4 up-regulation was a common characteristic of SPEM, HE4 staining in the mucosa of C57BL/6 mice infected with *Helicobacter felis* for 9 months was also evaluated. Prominent HE4 staining was observed in SPEM cells throughout the fundic mucosa in *Helicobacter felis*-infected mice (FIG. 9C).

Figure 9:
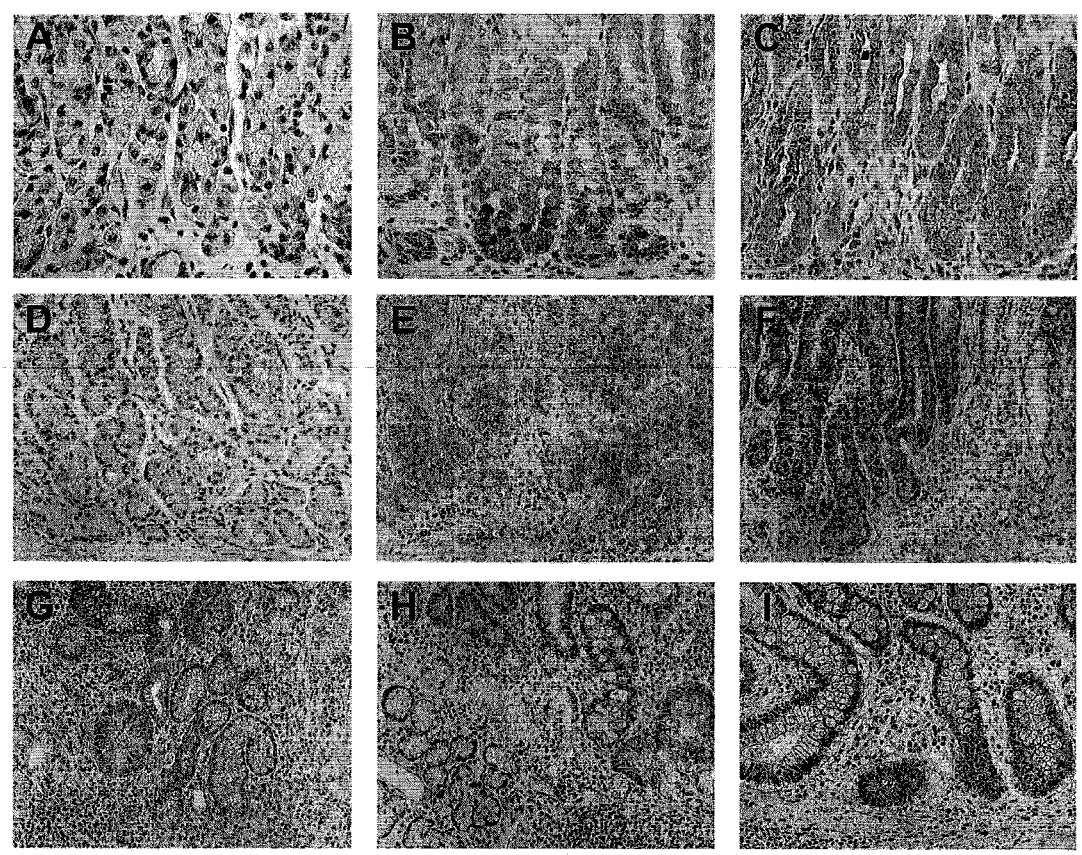
FIGS. 9A-9I are photomicrographs showing up-regulation of HE4 in both SPEM and goblet cell intestinal metaplasia. HE4 expression in gastric metaplasias from mice (9A-9C) and humans (9D-9I) was examined.
Figure 10:
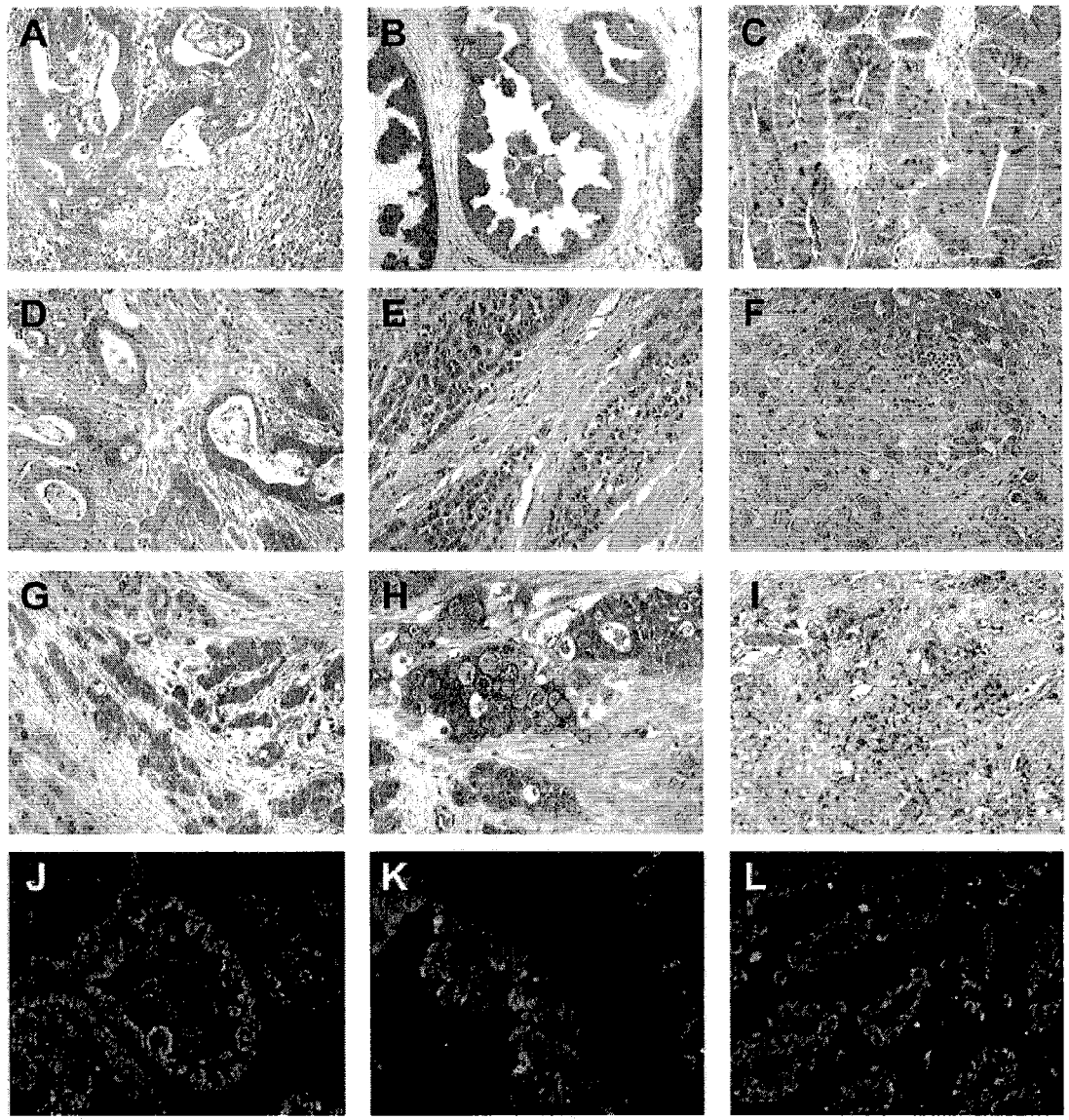
FIGS. 10A-10L are photomicrographs showing immunostaining for HE4 in human gastric adenocarcinoma. HE4 antibodies were used to stain sections of gastric adenocarcinomas with immunohistochemical detection with alkaline phosphatase conjugated secondary antibody and Vector Red chromogen.

Since the studies in mice suggested a strong association of HE4 expression with gastric metaplasia, the expression of HE4 in the human stomach was evaluated. As noted previously (Bingle L, Singleton V, Bingle C D. The putative ovarian tumour biomarker gene HE4 (WFDC2), is expressed in normal tissues and undergoes complex alternative splicing to yield multiple protein isoforms. Oncogene 2002; 21:2768-73) HE4 was not detected in the normal human fundic mucosa (FIG. 9D). Surprisingly, it was found that HE4 was strongly expressed in both SPEM and goblet cell intestinal metaplasia and also in transitional metaplastic changes (FIG. 9, E-I). Furthermore, tissue array analysis showed that HE4 was positive in all metaplastic lesions, including SPEM (FIG. 9E), SPEM and intestinal metaplasia transitional lesions (FIG. 9F), SPEM and intestinal metaplasia co-existing lesions (FIG. 9, G-H), and intestinal metaplasia (FIG. 9I). Given the strong expression of HE4 in human gastric metaplasias, the expression of HE4 in human gastric adenocarcinoma was also examined. In contrast with TFF2, which shows a general loss in gastric cancer, sustained expression of HE4 in 70% of well and moderately-differentiated intestinal type gastric adenocarcinoma was observed (FIG. 10, A-D). 20% of diffuse or poody differentiated tumors also showed HE4 staining (FIG. 10, E-F). The HE4 staining was especially strong in 80% of signet ring adenocarcinomas (FIG. 10, G-I). Similar results were observed with immunofluorescence staining, supporting the histochemical staining results for HE4 (FIG. 10, J-L). These results indicate that HE4 is a robust biomarker for the gastric pre-neoplasia and the neoplastic process.

DISCUSSION OF EXAMPLES

The loss of parietal cells, oxyntic atrophy, is a reliable correlate with gastric cancer in humans. The results presented in the present Examples suggest that the loss of parietal cells in gastrin deficient mice leads to the transdifferentiation of fundic chief cells into the mucous secreting SPEM lineage. Attendant with this transdifferentiation process, an up-regulation of genes involved in G1/S phase transition leading to re-entry of a population of cells into the cell cycle was observed. The transdifferentiation process was also associated with the up-regulation of a number of putative soluble regulators not usually present in the normal stomach mucosa. In particular, HE4 was up-regulated in gastric metaplasia in both mice and humans and its expression was maintained in gastric adenocarcinomas. Thus, examination of the process of transdifferentiation in mice has revealed a number of critical regulators relevant to the neoplastic process in humans.

While most views of the stomach mucosa have centered on lineage production from the normal progenitor zone in the neck of gastric fundic glands, the present investigations focus attention on a potential proliferative compartment at the bases of fundic glands induced following parietal cell loss (Nomura S, Yamaguchi H, Wang T C, Lee J R, Goldenring J R. Alterations in gastric mucosal lineages induced by acute oxyntic atrophy in wild type and gastrin deficient mice. Amer.J.Physiol. 2004). Without wishing to be bound by any particular theory, two explanations could account for this observation. First, a cryptic progenitor cell population may exist at the base of fundic glands, distinct from the normal progenitor region in the neck, which would be suppressed by mucosal differentiation factors released by parietal cells. Alternatively, SPEM may develop from transdifferentiation of chief cells. Previous studies have demonstrated that acute oxyntic atrophy leads to the observation of proliferating cells expressing Mist 1 and intrinsic factor, a biomarkers of differentiated chief cells in mice (Nomura S, Yamaguchi H, Wang T C, Lee J R, Goldenring J R. Alterations in gastric mucosal lineages induced by acute oxyntic atrophy in wild type and gastrin deficient mice. Amer.J.Physiol. 2004) (Nam K T, Varro A, Coffey R J, Goldenring J R. Potentiation of oxyntic atrophy-induced gastric metaplasia in amphiregulin-deficient mice. Gastroenterology 2007; 132:1804-19). Whereas intrinsic factor is expressed in rare pre-zymogenic cells, Mist1 is expressed only in mature chief cells (Ramsey V G Doherty J M, Chen C C, Stappenbeck T S, Konieczny S F, Mills J C. The maturation of mucus-secreting gastric epithelial progenitors into digestive-enzyme secreting zymogenic cells requires Mist1. Development 2007; 134:211-22). The present observation of Mist1-immunoreactive cells also expressing TFF2 supports chief cell transdifferentiation as the origin of SPEM, Nevertheless, these findings may also support a model compatible with both hypotheses. MCM3, which is required for unwinding of DNA during the G1/S transition was expressed not only in normal progenitor cells in the gastric gland neck, but also in a small population of intrinsic factor-immunoreactive chief cells at the bases of fundic glands. Thus, a subpopulation of chief cells may have the potential for transdifferentiation, in effect a cryptic progenitor population. Still, the rapid emergence of SPEM at the base of gastric glands in the gastrin-deficient mice after DMP-777 treatment suggests that a broader transdifferentiative process is required to account for the amount of SPEM observed after only 1 or 3 days of treatment.

The gene microarray studies of microdissected SPEM cells also support a molecular phenotype for chief cell transdifferentiation. The rapid up-regulation after only a single dose of DMP-777 of a cohort of gene transcripts related to the initiation of the G1/S cell cycle transition was observed. MCM proteins (MCM2-7) are transcribed at M/G1 and assemble into a DNA helicase responsible for unwinding chromatin prior to DNA synthesis (Braun K A, Breeden L L. Nascent transcription of MCM2-7 is important for nuclear localization of the minichromosome maintenance complex in G1. Mol Biol Cell 2007; 18:1447-56). MCM3 is ubiquitinated specifically in G2/M and degraded as cells exit mitosis. Still, while MCM proteins are broadly up-regulated in SPEM at the bases of fundic glands in DMP-777-treated mice, only a subset of cells entering the proliferative cycle have been observed. Thus, although some cells are re-entering the cell cycle, the observation of the up-regulation of a number of proteins involved in G1/S transition is also consistent with an alternative hypothesis. Transdifferentiation would require a major alteration in the compendium of transcripts expressed in cells without necessarily going through a proliferative cycle. Such a change in transcripts would require the unwinding of DNA, just as at the G1/S cell cycle interface. Thus, the up-regulation of proteins involved in DNA remodeling may reflect more the process of transdifferentiation than activation of proliferation. The sustained expression of MCM3 in DMP-777 treated mice supports the concept of an alteration of the compendium of transcripts during transdifferentiation, with only limited progression through the cell cycle.

The findings presented herein also suggest that transdifferentiation leads to up-regulation of gene transcripts specific for mucous cell metaplasia. The transdifferentiation of zymogenic cells to mucous metaplasia may be a general mechanism underlying pre-neoplastic transition in the upper gastrointestinal tract. Means, et al. have demonstrated that over-expression of TGFα leads to the transdifferentiation of pancreatic zymogen cells into mucous secreting metaplastic cells (Means A L, Meszoely I M, Suzuki K, Miyamoto Y, Rustgi A K, Coffey R J, Jr., Wright C V, Stoffers D A, Leach S D. Pancreatic epithelial plasticity mediated by acinar cell transdifferentiation and generation of nestin-positive intermediates, Development 2005; 132:3767-76). Acinar cell transdifferentiation contributes to pre-neoplastic PANIN lesion formation in the pancreas (Zhu L, Shi G, Schmidt C M, Hruban R H, Konieczny S F. Acinar cells contribute to the molecular heterogeneity of pancreatic intraepithelial neoplasia. Am J Pathol 2007; 171:263-73). Likewise, loss of parietal cells may elicit the transdifferentiation of gastric zymogen-secreting chief cells. Nevertheless, the present findings also suggest that attendant with the transdifferentiation process, the mucous cell metaplasia up-regulates specific secreted mucosal factors, including HE4, WDNM1, IL1RN and Epiregulin. IL1RN has been implicated in a number of neoplastic processes (Machado J C, Pharoah P, Sousa S, Carvalho R, Oliveira C, Figueiredo C, Amorim A, Seruca R, Caldas C, Carneiro F, Sobrinho-Simoes M. Interleukin 1B and interleukin 1RN polymorphisms are associated with increased risk of gastric carcinoma. Gastroenterology 2001; 121:823-9). Similarly, Epiregulin, an EGF receptor ligand family member with affinity for Erb4, is associated with more aggressive cancer metastasis (Gupta G P, Nguyen D X, Chiang A C, Bos P D, Kim J Y, Nadal C, Gomis R R, Manova-Todorova K, Massague J. Mediators of vascular remodelling co-opted for sequential steps in lung metastasis. Nature 2007; 446:765-70). HE4 is up-regulated early in the development of ovarian cancer and may serve as a biomarker of ovarian neoplasia (Drapkin R, von Horsten H H, Lin Y, Mok S C, Crum C P, Welch W R, Hecht J L. Human epididymis protein 4 (HE4) is a secreted glycoprotein that is overexpressed by serous and endometrioid ovarian carinomas, but has not previously been reported in upper GI cancers. Cancer Res 2005; 65:2162-9). HE4 is not expressed in the normal human gastric mucosa. Surprisingly, the present data demonstrate prominent up-regulation of HE4 expression in both intestinal metaplasia and SPEM. Importantly, HE4 expression was maintained in the vast majority of differentiated gastric adenocarcinomas. The current Examples therefore show that factors up-regulated in the process of transdifferentiation to produce SPEM also may serve as surrogate biomarkers of gastric pre-neoplasia and neoplasia.

Figure 11:
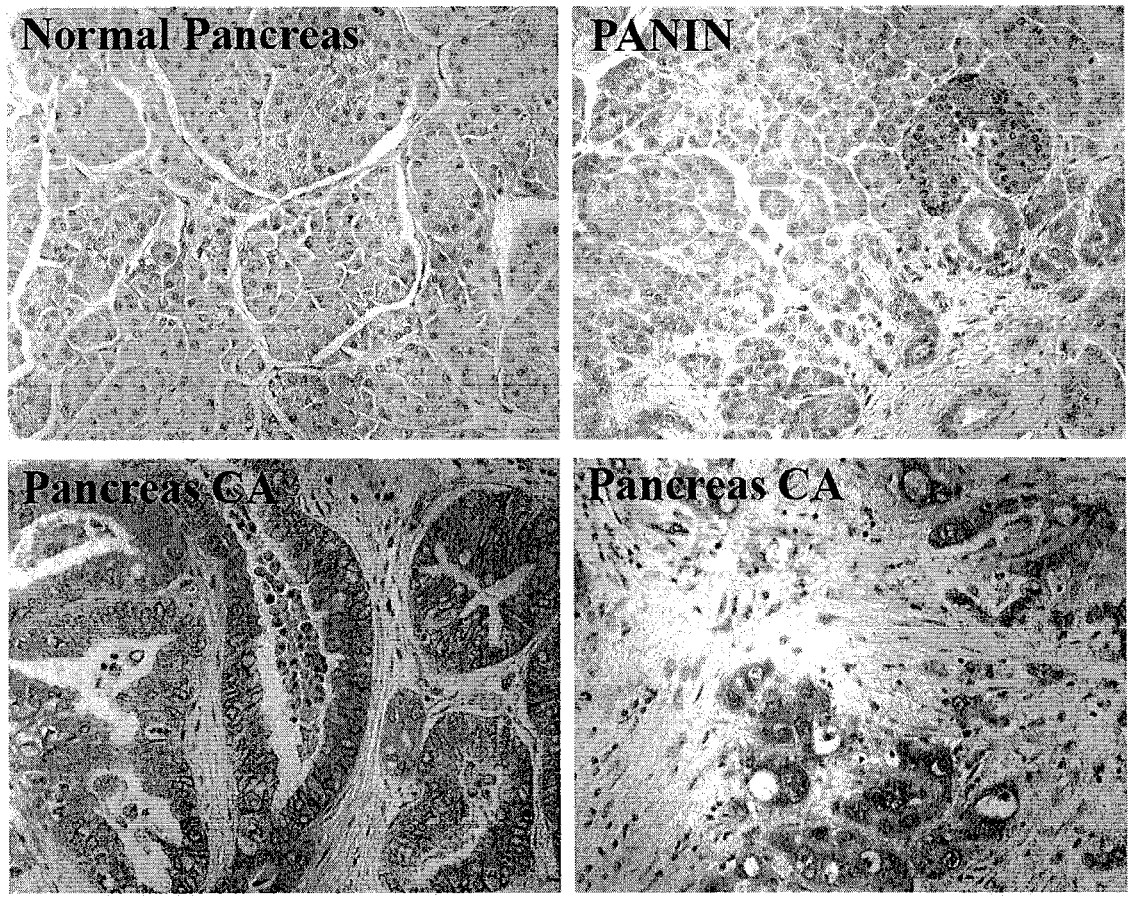
FIG. 11 is a series of photomicrographs showing immunostaining for HE4 in diseased and normal human pancreas. Sections of normal human pancreas (upper left), human pancreas with pre-neoplastic PANIN lesions (upper right) and human pancreas with either well differentiated pancreatic adenocarcinoma (lower left) or poorly differentiated pancreatic adenocarcinoma (lower right) were stained with antibodies against HE4.

The present data also demonstrate increased expression of HE4 in PANIN lesions and pancreatic adenocarcinoma (FIG. 11). HE4 was not detected in the normal exocrine pancreas However, strong staining for HE4 in both PANIN lesions and pancreatic adenocarcinoma was observed (FIG. 11).

In summary, while previous views have suggested that gastric metaplasia originates from normal mucosal progenitor cells, the present Examples indicate that the loss of parietal cells from the gastric fundic mucosa induces alterations in the transcriptional profile of chief cells leading to changes in the cellular secretory phenotype and transdifferentiation into a mucous cell metaplasia. Attendant with these changes, particular soluble regulators such as HE4 and the other biomarkers disclosed herein (Table 1) are up-regulated in metaplasia and represent characteristic putative biomarkers for the metaplastic and pre-neoplastic process.

It will be understood that various details of the presently-disclosed subject matter can be changed without departing from the scope of the presently-disclosed subject matter. Furthermore, the foregoing description is for the purpose of illustration only, and not for the purpose of limitation.

REFERENCES

Aitola M, Sadek C M, Gustafsson J A, Pelto-Huikko M. Aint/Tacc3 is highly expressed in proliferating mouse tissues during development, spermatogenesis, and oogenesis. J Histochem Cytochem 2003; 51:455-69.

Beauchamp R D, Barnard J A, McCutchen C M, Cherner J A, Coffey R J, Jr. Localization of transforming growth factor alpha and its receptor in gastric mucosal cells. J.Clin.Invest. 1989; 84:1017-1023.

Biankin, A. V., Kench, J. G., Dijkman, F. P., Biankin, S. A., and Henshall, S. M. Molecular pathogenesis of precursor lesions of pancreatic ductal adenocarcinoma. Pathology 2003; 35:14-24.

Bingle L, Singleton V, Bingle C D. The putative ovarian tumour marker gene HE4 (WFDC2), is expressed in normal tissues and undergoes complex alternative splicing to yield multiple protein isoforms. Oncogene 2002; 21:2768-73.

Blaser, M. and Parsonnet, J. Parasitism by the bacterium *Helicobacter pylori* leads to altered gastric homeostasis and neoplasia. J.Clin.Invest. 1994; 94:4-8.

Bouchard, D., Morisset, D., Bourbonnais, Y., and Tremblay, G. M. Proteins with whey-acidic-protein motifs and cancer. Lancet Oncol 2006; 7:167-174.

Braun K A, Breeden L L. Nascent transcription of MCM2-7 is important for nuclear localization of the minichromosome maintenance complex in G1. Mol Biol Cell 2007; 18:1447-56.

Cameron, A. J., Lomboy, C. T. Pera, M., and Carpenter, H. A. Adenocarcinoma of the esophagogastric junction and Barrett's esophagus. Gastroenterology 1995; 109:1541-1546.

Correa, P. A human model of gastric carcinogenesis. Cancer Res. 1988; 48:3554-3560.

Dhar, D. K., Wang, T. C., Maruyama, R., Udagawa, J., Kubota, H., Fuji, T., Tachibana, M., Ono, T., Otani, H., and Nagasue, N. Expression of cytoplasmic TFF2 is a biomarker of tumor metastasis and negative prognostic factor in gastric cancer. Lab Invest 2003; 83:1343-1352.

Dinis-Ribeiro M, da Costa-Pereira A, Lopes C, Barbosa J, Guilherme M, Moreira-Dias L, Lomba-Viana H, Silva R, Abreu N, Lomba-Viana R. Validity of serum pepsinogen I/II ratio for the diagnosis of gastric epithelial dysplasia and intestinal metaplasia during the follow-up of patients at risk for intestinal-type gastric adenocarcinoma. Neoplasia 2004; 6(5):449-56.

El-Zimaity, H M T, Ota, H, Graham, D Y, Akamatsu, T, and Katsuyama, T Patterns of gastric atrophy in intestinal type gastric carcinoma, *Cancer* 2002; 94:1428-36.

Filipe, M. I., Munoz, N., Matko, I., Kato, I., Pome-Kim, V., Juersek, A, Teuchmann, S., Benz, M., Prijon, T. Intestinal metaplasia types and the risk of gastric cancer: a cohort study in Slovenia, Int J Cancer. 1994; 57:324-329.

Gait, M. J., ed., Oligonucleotide Synthesis, 1984.

Galgano, M. T., Hampton, G. M., and Frierson, H. F. Comprehensive analysis of HE4 expression in normal and malignant human tissues. *Mod Pathol* 2006; 19:847-853.

Glover, ed., DNA Cloning, Volumes I and II, 1985.

Goldenring J R, Ray G S, Coffey R J, Meunier P C, Haley P J, Barnes T B, Car B D. Reversible drug-induced oxyntic atrophy in rats. Gastroenterology. 2000; 118:1080-1093.

Halldorsdottir, et al. Spasmolytic polypeptide expressing metaplasia (SPEM) associated with gastric cancer in Iceland. *Dig.Dis.Sci.* 48:431-441.

Hames & Higgins, eds., Nucleic Acid Hybridization, 1984.

Hames & Higgins, eds., Transcription and Translation, 1984.

Hattori, T. Development of adenocarcinomas in the stomach. Cancer 1986; 57:1528-1534.

Hellstrom, I., Raycraft, J., Hayden-Ledbetter, M., Ledbetter, J. A., Schummer, M., McIntosh, M., Drescher, C., Urban, N., and Hellstrom, K. E. The HE4 (WFDC2) protein is a biomarker for ovarian carcinoma. Cancer Res 2003; 63:3695-3700.

Houghton J, Stoicov C, Nomura S, Carlson J, Li H, Rogers A B, Fox J G, Goldenring J R, Wang T C. Gastric cancer originating from bone marrow derived cells. Science 2004; In Press.

Karam S M, Leblond C P. Dynamics of epithelial cells in the corpus of the mouse stomach, III. Inward migration of neck cells followed by progressive transformation into zymogenic cells. Anat.Rec. 1993; 236:297-313.

Leys C M, Nomura S, Rudzinski E, Kaminishi M, Montgomery E, Washington M K, Goldenring J R. Expression of Pdx-1 in human gastric metaplasia and gastric adenocarcinoma. Hum Pathol 2006; 37:1162-8.

Mayer and Walker, eds. Immunochemical Methods In Cell And Molecular Biology, Academic Press, London, 1987.

Means A L, Meszoely I M, Suzuki K, Miyamoto Y, Rustgi A K, Coffey R J, Jr., Wright C V, Stoffers D A, Leach S D. Pancreatic epithelial plasticity mediated by acinar cell transdifferentiation and generation of nestin-positive intermediates. Development 2005; 132:3767-76.

Miller and Calos, eds., Gene Transfer Vectors For Mammalian Cells, Cold Spring Harbor Laboratory, 1987.

Nam K T, Varro A, Coffey R J, Goldenring J R. Potentiation of oxyntic atrophy-induced gastric metaplasia in amphiregulin-deficient mice. Gastroenterology 2007; 132:1804-19.

Nomura S, Baxter S, Yamaguchi T, Leys C, Vartapetian A B, Fox J G, Lee J R, Wang T C, Goldenring J R. Relationship of spasmolytic polypeptide expressing metaplasia (SPEM) to pre-neoplasia in *H. felis*-infected mice. Gastroenterology 2004; 127:582-594.

Nomura, S., Settle, S. H., Leys, C., Means, A. L., Peek, R. M., Jr., Leach, S. D., Wright, C. V. E., Coffey, R. J., and Goldenring, J. R. Evidence for repatterning of the gastric fundic epithelium associated with Menetrier's disease and TGFa overexpression. Gastroenterology 2005; 128:1292-1305.

Nomura, S., Yamaguchi, H., Wang, T. C., Lee, J. R., and Goldenring, J. R. Alterations in gastric mucosal lineages induced by acute oxyntic atrophy in wild type and gastrin deficient mice. Amer.J.Physiol. 2004; 288:G362-G375.

Ogawa, M., Nomura, S., Wang, T. C., and Goldenring, J. R. Altered metaplastic response of waved-2 EGF receptor mutant mice to acute oxyntic atrophy. Am J Physio. 2006; 290:G793-G804.

Oishi Y, Kiyohara Y, Kubo M, Tanaka K, Tanizaki Y, Ninomiya T, Doi Y. Shikata K, Yonemoto K, Shirota T, Matsumoto T, Iida M. The serum pepsinogen test as a predictor of gastric cancer: the Hisayama study. Am J Epidemiol. 2006; 163(7):629-37.

Parsonnet J, Friedman G D, Vandersteen D P, Chang Y, Vogelman J H, Orentreich N, Sibley R K. *Helicobacter pylori* infection and the risk of gastric cancer. New Eng.J.Med. 1991; 325:1127-1131.

Perbal, A Practical Guide To Molecular Cloning; See Methods In Enzymology (1984, Academic Press, Inc., N.Y.).

Pisani P, Bray F, Parkin D M. Estimates of the world-wide prevalence of cancer for 25 sites in the adult population. Int J Cancer 2002; 97:72-81.

R. I. Freshney, Alan R. Liss, Inc., Culture Of Animal Cells, 1987.

Ramsey V G, Doherty J M, Chen C C, Stappenbeck T S, Konieczny S F, Mills J C. The maturation of mucus-secreting gastric epithelial progenitors into digestive-enzyme secreting zymogenic cells requires Mist1. Development 2007; 134: 211-22.

Sambrook, Fritsch and Maniatis. eds. Molecular Cloning A Laboratory Manual (1989), 2nd Ed., ed. by Cold Spring Harbor Laboratory Press, Chapters 16 and 17.

Schmidt P H, Lee J R, Joshi V, Playford R J, Poulsom R, Wright N A, Goldenring J R. Identification of a metaplastic cell lineage associated with human gastric adenocarcinoma. Lab.Invest. 1999; 79:639-646.

Smith, V. C., Genta, R. M. Role of *Helicobacter pylori* gastritis in gastric atrophy, intestinal metaplasia, and gastric neoplasia, Microsc Res Tech. 2000; 48: 313-20.

Stepan V, Ramamoorthy S, Nitsche H, Zavros Y. Merchant J L. Todisco A. Regulation and function of the sonic hedgehog signal transduction pathway in isolated gastric parietal cells. J Biol Chem 2005; 280:15700-8.

U.S. Patent Application Publication No. 2003/0108965.

U.S. Pat. No. 4,683,195.

U.S. Pat. No. 5,480,792.

U.S. Pat. No. 5,525,524.

U.S. Pat. No. 5,631,171.

U.S. Pat. No. 5,679,526.

U.S. Pat. No. 5,824,799.

U.S. Pat. No. 5,851,776.

U.S. Pat. No. 5,885,527.

U.S. Pat. No. 5,922,615.

U.S. Pat. No. 5,939,272.

U.S. Pat. No. 5,947,124.

U.S. Pat. No. 5,955,377.

U.S. Pat. No. 5,985,579.

U.S. Pat. No. 6,019,944.

U.S. Pat. No. 6,113,855.

U.S. Pat. No. 6,143,576.

U.S. Pat. No. 6,890,763.

U.S. Pat. No. 6,925,389.

U.S. Pat. No. 6,989,100.

Wang T C, Dangler C A, Chen D, Goldenring J R, Koh T, Raychowdhury R, Coffey R J, Ito S, Varro A, Dockray G J, Fox J G. Synergistic interaction between hypergastrinemia and *Helicobacter* infection in a mouse model of gastric cancer. Gastroenterology 2000; 118:36-47.

Weir and Blackwell, eds. Handbook Of Experimental Immunology, Volumes I-IV, 1986.

Wu et al., eds., Methods In Enzymology, Vols. 154 and 155, Academic Press Inc., N.Y.

Yamaguchi, H., Goldenring, J. R., Kaminishi, M., and Lee, J. R. Association of spasmolytic polypeptide expressing metaplasia (SPEM) with carcinogen administration and oxyntic atrophy in rats, Lab. Invest, 2002; 82:-1045-1052.

Zhang B, Kirov S, Snoddy J. WebGestalt: an integrated system for exploring gene sets in various biological contexts. Nucleic Acids Res 2005; 33:W741 -8.

Zhu L, Shi G, Schmidt C M, Hruban R H, Konieczny S F. Acinar cells contribute to the molecular heterogeneity of pancreatic intraepithelial neoplasia. Am J Pathol 2007; 171: 263-73.

What is claimed is:

1. A method for diagnosing an upper gastrointestinal (GI) cancer in a subject, comprising:
   (a) providing a biological sample from the subject;
   (b) determining an amount in the sample of at least two biomarkers, wherein the at least two biomarkers comprise HE4 and EREG; and
   (c) comparing the amount in the sample of the at least two biomarkers, if present, to a control level of the at least two biomarkers, wherein the subject is diagnosed as having an upper GI cancer if there is a measurable difference in the amount of the at least two biomarkers in the sample as compared to the control level, wherein the upper GI cancer is gastric adenocarcinoma or gastric pre-neoplasia.

2. The method of claim 1, wherein the biological sample comprises blood, serum, plasma, gastric secretions, an upper GI biopsy sample, microdissected cells from an upper GI biopsy, upper GI cells sloughed into the GI lumen, and upper GI cells recovered from stool.

3. The method of claim 1, comprising further determining an amount in the sample of a TFF2 biomarker.

4. The method of claim 1, wherein determining the amount of the at least two biomarkers comprises one or more techniques selected from:
   (a) determining an amount of mRNA of the at least two biomarkers in the biological sample using an RNA measuring assay; and
   (b) determining an amount of a polypeptide of the at least two biomarkers in the biological sample using a protein measuring assay.

5. The method of claim 4, wherein the RNA measuring assay comprises an array of RNA hybridization probes or a quantitative polymerase chain reaction assay.

6. The method of claim 4, wherein the protein measuring assay comprises mass spectrometry (MS) analysis, immunoassay analysis, or both.

7. The method of claim 6, wherein the immunoassay analysis comprises one or more antibodies that selectively bind at least two biomarkers.

8. The method of claim 1, further comprising selecting a treatment or modifying a treatment for the upper GI cancer based on the amount of the at least two biomarkers determined.

9. A method for determining whether to initiate or continue treatment of an upper gastrointestinal (GI) cancer in a subject, comprising:
   (a) providing a series of biological samples over a time period from the subject;
   (b) analyzing the series of biological samples to determine an amount in each of the biological samples of at least two biomarkers, wherein the at least two biomarkers comprise HE4 and EREG; and
   (c) determining any measurable change in the amount of the at least two biomarkers in each of the biological samples to thereby determine whether to initiate or continue the therapy of the upper GI cancer, wherein the upper GI cancer is gastric adenocarcinoma or gastric pre-neoplasia.

10. The method of claim 9, wherein the biological sample comprises blood, serum, plasma, gastric secretions, an upper GI biopsy sample, microdissected cells from an upper GI biopsy, upper GI cells sloughed into the GI lumen, and upper GI cells recovered from stool.

11. The method of claim 9, comprising further analyzing the series of biological samples to determine an amount of a TFF2 biomarker in each of the biological samples.

12. The method of claim 9, wherein the series of biological samples comprises a first biological sample collected prior to initiation of the treatment for the upper GI cancer and a second biological sample collected after initiation of the treatment.

13. The method of claim 9, wherein analyzing the series of biological samples to determine the amount of the at least two biomarkers in each of the samples comprises one or more techniques selected from:
   (a) determining an amount of mRNA of the at least two biomarkers in each of the biological samples using an RNA measuring assay; and
   (b) determining an amount of a polypeptide of the at least two biomarkers in each of the biological samples using a protein measuring assay.

14. The method of claim 13, wherein the RNA measuring assay comprises an array of RNA hybridization probes or a quantitative polymerase chain reaction assay.

15. The method of claim 13, wherein the protein measuring assay comprises mass spectrometry (MS) analysis, immunoassay analysis, or both.

16. The method of claim 15, wherein the immunoassay analysis comprises one or more antibodies that selectively bind the at least two biomarkers.

17. The method of claim 1, further comprising providing an apparatus capable of detecting the at least two biomarkers.

18. The method of claim 1, further comprising providing probes for selectively binding each of the at least two biomarkers.

19. The method of claim 18, further comprising measuring an amount of a biomarker-bound probe for each of the at least two biomarkers.

20. The method of claim 9, further comprising providing an apparatus capable of detecting the at least two biomarkers.

21. The method of claim 9, further comprising providing a probe for selectively binding each of the at least two biomarkers.

22. The method of claim 21, further comprising measuring an amount of a biomarker-bound probe for each of the at least two biomarkers.

23. The method of claim 1, further comprising determining an amount in the sample of at least two biomarkers selected from the group consisting of LGALS3, IL1RN, TRIP13, FIGNL1, CRIP1, S100A4, EXOSC8, EXPI, BRRN1, NELF, TMEM40, and TMEM109.

24. The method of claim 9, further comprising determining an amount in the sample of at least two biomarkers selected from the group consisting of LGALS3, IL1RN, TRIP13, FIGNL1, CRIP1, S100A4, EXOSC8, EXPI, BRRN1, NELF, TMEM40, and TMEM109.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial
<220> FEATURE:
<223> OTHER INFORMATION: Artificially-generated PCR sense primer
      sequence specific for GAPDH

<400> SEQUENCE: 1
tgacgtgccg cctggagaaa                                              20

<210> SEQ ID NO 2
<211> LENGTH: 21
<212> TYPE: DNA
<213> ORGANISM: Artificial
<220> FEATURE:
<223> OTHER INFORMATION: Artificially-generated PCR antisense primer
      sequence specific for GAPDH

<400> SEQUENCE: 2
ccggcatcga aggtggaaga g                                            21

<210> SEQ ID NO 3
<211> LENGTH: 21
<212> TYPE: DNA
<213> ORGANISM: Artificial
<220> FEATURE:
<223> OTHER INFORMATION: Artificially-generated PCR sense primer
      sequence specific for MCM3

<400> SEQUENCE: 3
gcgcagagag actacttgga c                                            21

<210> SEQ ID NO 4
<211> LENGTH: 16
<212> TYPE: DNA
<213> ORGANISM: Artificial
<220> FEATURE:
<223> OTHER INFORMATION: Artificially-generated PCR antisense primer
      sequence specific for MCM3

<400> SEQUENCE: 4
tgcttggcgt aggtgg                                                  16

<210> SEQ ID NO 5
<211> LENGTH: 21
<212> TYPE: DNA
<213> ORGANISM: Artificial
<220> FEATURE:
<223> OTHER INFORMATION: Artificially-generated PCR sense primer
      sequence specific for MCM5

<400> SEQUENCE: 5
gcggcattac aacctgggtg a                                            21

<210> SEQ ID NO 6
<211> LENGTH: 21
<212> TYPE: DNA
<213> ORGANISM: Artificial
<220> FEATURE:
<223> OTHER INFORMATION: Artificially-generated PCR antisense primer
      sequence specific for MCM5

<400> SEQUENCE: 6

```
acgggctggc atctgacttg a                                    21
```

<210> SEQ ID NO 7
<211> LENGTH: 20
<212> TYPE: DNA
<213> ORGANISM: Artificial
<220> FEATURE:
<223> OTHER INFORMATION: Artificially-generated PCR sense primer
      sequence specific for MCM7

<400> SEQUENCE: 7

```
cacgctcaat gcccgatgct                                      20
```

<210> SEQ ID NO 8
<211> LENGTH: 21
<212> TYPE: DNA
<213> ORGANISM: Artificial
<220> FEATURE:
<223> OTHER INFORMATION: Artificially-generated PCR antisense primer
      sequence specific for MCM7

<400> SEQUENCE: 8

```
ttgtctctgt cgggccggtc t                                    21
```

<210> SEQ ID NO 9
<211> LENGTH: 21
<212> TYPE: DNA
<213> ORGANISM: Artificial
<220> FEATURE:
<223> OTHER INFORMATION: Artificially-generated PCR sense primer
      sequence specific for ST3Gal6

<400> SEQUENCE: 9

```
catatatcac cagcgaagca g                                    21
```

<210> SEQ ID NO 10
<211> LENGTH: 20
<212> TYPE: DNA
<213> ORGANISM: Artificial
<220> FEATURE:
<223> OTHER INFORMATION: Artificially-generated PCR antisense primer
      sequence specific for ST3Gal6

<400> SEQUENCE: 10

```
tggcattccc gtagtagtgt                                      20
```

<210> SEQ ID NO 11
<211> LENGTH: 18
<212> TYPE: DNA
<213> ORGANISM: Artificial
<220> FEATURE:
<223> OTHER INFORMATION: Artificially-generated PCR sense primer
      sequence specific for ATF3

<400> SEQUENCE: 11

```
gatgcaacgc gctcccag                                        18
```

<210> SEQ ID NO 12
<211> LENGTH: 21
<212> TYPE: DNA
<213> ORGANISM: Artificial
<220> FEATURE:
<223> OTHER INFORMATION: Artificially-generated PCR antisense primer
      sequence specific for ATF3

<400> SEQUENCE: 12
ggcggccagg gtccagagaa c                                              21

<210> SEQ ID NO 13
<211> LENGTH: 19
<212> TYPE: DNA
<213> ORGANISM: Artificial
<220> FEATURE:
<223> OTHER INFORMATION: Artificially-generated PCR sense primer
      sequence specific for HE4

<400> SEQUENCE: 13
tgcctgcctg tcgcctctg                                                19

<210> SEQ ID NO 14
<211> LENGTH: 21
<212> TYPE: DNA
<213> ORGANISM: Artificial
<220> FEATURE:
<223> OTHER INFORMATION: Artificially-generated PCR antisense primer
      sequence specific for HE4

<400> SEQUENCE: 14
tgtccgcaca gtccttgtcc a                                             21

<210> SEQ ID NO 15
<211> LENGTH: 21
<212> TYPE: DNA
<213> ORGANISM: Artificial
<220> FEATURE:
<223> OTHER INFORMATION: Artificially-generated PCR sense primer
      sequence specific for IL1RN

<400> SEQUENCE: 15
ttggcctagg tgtcttctgc t                                             21

<210> SEQ ID NO 16
<211> LENGTH: 20
<212> TYPE: DNA
<213> ORGANISM: Artificial
<220> FEATURE:
<223> OTHER INFORMATION: Artificially-generated PCR antisense primer
      sequence specific for IL1RN

<400> SEQUENCE: 16
tatgtgatgc cctggtggtt                                               20

<210> SEQ ID NO 17
<211> LENGTH: 20
<212> TYPE: DNA
<213> ORGANISM: Artificial
<220> FEATURE:
<223> OTHER INFORMATION: Artificially-generated PCR sense primer
      sequence specific for TFF2

<400> SEQUENCE: 17
tgctttgatc ttggatgctg                                               20

<210> SEQ ID NO 18
<211> LENGTH: 20
<212> TYPE: DNA
<213> ORGANISM: Artificial
<220> FEATURE:

```
<223> OTHER INFORMATION: Artificially-generated PCR antisense primer
      sequence specific for TFF2

<400> SEQUENCE: 18
ggaaaagcag cagtttcgac                                              20
```